US010493276B2

(12) United States Patent
Moffitt et al.

(10) Patent No.: US 10,493,276 B2
(45) Date of Patent: Dec. 3, 2019

(54) NEUROMODULATION SPECIFIC TO OBJECTIVE FUNCTION OF MODULATION FIELD FOR TARGETED TISSUE

(71) Applicant: Boston Scientific Neuromodulation Corporation, Valencia, CA (US)

(72) Inventors: Michael A. Moffitt, Valencia, CA (US); Changfang Zhu, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 343 days.

(21) Appl. No.: 14/860,961

(22) Filed: Sep. 22, 2015

(65) Prior Publication Data

US 2016/0082251 A1 Mar. 24, 2016

Related U.S. Application Data

(60) Provisional application No. 62/054,081, filed on Sep. 23, 2014.

(51) Int. Cl.
*A61N 1/05* (2006.01)
*A61N 1/36* (2006.01)
*A61N 1/372* (2006.01)

(52) U.S. Cl.
CPC ....... *A61N 1/36071* (2013.01); *A61N 1/0551* (2013.01); *A61N 1/3605* (2013.01);
(Continued)

(58) Field of Classification Search
CPC ........................ A61N 1/36071; A61N 1/0551
See application file for complete search history.

(56) References Cited

U.S. PATENT DOCUMENTS 5,501,703 A 3/1996 Holsheimer et al.
6,516,227 B1 2/2003 Meadows et al.
(Continued)

FOREIGN PATENT DOCUMENTS

AU 2015321559 B2 1/2019
CN 1138829 A 12/1996
(Continued)

OTHER PUBLICATIONS

Rao, Prakash, et al., "Technique for Linking Electrodes Together During Programming of Neurostimulation System", U.S. Appl. No. 61/561,760, filed Nov. 18, 2011.
(Continued)

*Primary Examiner* — Michael J D Abreu
(74) *Attorney, Agent, or Firm* — Schwegman Lundberg & Woessner, P.A.

(57) ABSTRACT

An example of a system may include electrodes on at least one lead configured to be operationally positioned for use in modulating a volume of neural tissue, where the neural tissue has an activation function. The system may further include a neural modulation generator configured to deliver energy using at least some electrodes to generate a modulation field within the volume of neural tissue. The neural modulation generator may be configured to use a programmed modulation parameter set to generate the modulation field. The programmed modulation parameter set having values selected to control energy delivery using the at least some electrodes to achieve an objective function specific to the activation function of the volume of neural tissue to promote uniformity of a response to the modulation field in the volume of neural tissue along a span of the at least one lead.

20 Claims, 20 Drawing Sheets

(52) U.S. Cl.
CPC ..... *A61N 1/36128* (2013.01); *A61N 1/36153* (2013.01); *A61N 1/36164* (2013.01); *A61N 1/37247* (2013.01)

(56) References Cited

U.S. PATENT DOCUMENTS

| | | | |
|---|---|---|---|
| 6,675,046 | B2 | 1/2004 | Holsheimer |
| 6,895,280 | B2 | 5/2005 | Meadows et al. |
| 6,993,384 | B2 | 1/2006 | Bradley et al. |
| 7,317,948 | B1 | 1/2008 | King et al. |
| 7,333,857 | B2 | 2/2008 | Campbell |
| 7,539,538 | B2 | 5/2009 | Parramon et al. |
| 7,650,184 | B2 | 1/2010 | Walter |
| 7,979,133 | B2 | 7/2011 | Feler et al. |
| 8,019,439 | B2 | 9/2011 | Kuzma et al. |
| 8,224,453 | B2 | 7/2012 | De Ridder |
| 8,255,057 | B2 | 8/2012 | Fang et al. |
| 8,355,797 | B2 | 1/2013 | Caparso et al. |
| 8,380,318 | B2 | 2/2013 | Kishawi et al. |
| 8,455,716 | B2 | 6/2013 | Huang et al. |
| 8,504,147 | B2 | 8/2013 | Deem et al. |
| 8,615,300 | B2 | 12/2013 | Feler et al. |
| 8,649,874 | B2 | 2/2014 | Alataris et al. |
| 8,670,831 | B2 | 3/2014 | Wacnik et al. |
| 8,676,329 | B2 | 3/2014 | Wacnik et al. |
| 8,676,331 | B2 | 3/2014 | Parker |
| 8,731,675 | B2 | 5/2014 | Ranu et al. |
| 8,751,009 | B2 | 6/2014 | Wacnik |
| 2003/0139781 | A1 | 7/2003 | Bradley et al. |
| 2007/0150036 | A1 | 6/2007 | Anderson |
| 2008/0188909 | A1 | 8/2008 | Bradley |
| 2008/0215119 | A1 | 9/2008 | Woods et al. |
| 2009/0204173 | A1 | 8/2009 | Fang et al. |
| 2010/0010566 | A1 | 1/2010 | Thacker et al. |
| 2010/0121409 | A1 | 5/2010 | Kothandaraman et al. |
| 2010/0249875 | A1 | 9/2010 | Kishawi et al. |
| 2010/0274312 | A1 | 10/2010 | Alataris et al. |
| 2010/0274314 | A1 | 10/2010 | Alataris et al. |
| 2010/0274315 | A1 | 10/2010 | Alataris et al. |
| 2010/0274317 | A1 | 10/2010 | Parker et al. |
| 2010/0274318 | A1 | 10/2010 | Walker et al. |
| 2010/0274326 | A1 | 10/2010 | Chitre et al. |
| 2011/0270360 | A1* | 11/2011 | Harris ............... A61N 1/36 607/62 |
| 2012/0059446 | A1 | 3/2012 | Wallace et al. |
| 2012/0083709 | A1 | 4/2012 | Parker et al. |
| 2012/0253422 | A1 | 10/2012 | Thacker et al. |
| 2012/0265279 | A1 | 10/2012 | Zhu et al. |
| 2012/0283797 | A1 | 11/2012 | De Ridder |
| 2012/0290041 | A1 | 11/2012 | Kim et al. |
| 2013/0066411 | A1 | 3/2013 | Thacker et al. |
| 2013/0116752 | A1 | 5/2013 | Parker et al. |
| 2013/0184792 | A1* | 7/2013 | Simon ............... A61N 1/36025 607/115 |
| 2013/0268021 | A1 | 10/2013 | Moffitt |
| 2013/0296975 | A1 | 11/2013 | Lee et al. |
| 2014/0081349 | A1 | 3/2014 | Lee et al. |
| 2014/0243943 | A1* | 8/2014 | Rao ............... A61N 1/36071 607/116 |
| 2014/0277267 | A1* | 9/2014 | Vansickle ......... A61N 1/36071 607/46 |
| 2016/0045740 | A1* | 2/2016 | Rezai ............... A61N 1/3605 607/45 |

FOREIGN PATENT DOCUMENTS

| | | |
|---|---|---|
| CN | 102946941 A | 2/2013 |
| CN | 106687174 A | 5/2017 |
| JP | 2017529173 A | 10/2017 |
| WO | WO-2006029257 A2 | 3/2006 |
| WO | WO-2006135791 A2 | 12/2006 |
| WO | WO-2014145222 A2 | 9/2014 |
| WO | WO-2016048951 A1 | 3/2016 |

OTHER PUBLICATIONS

Vansickle, Dennis Allen, et al., "Neuromodulation System and Method for Transitioning Between Programming Modes", U.S. Appl. No. 14/214,752, filed Mar. 15, 2014.

Vansickle, Dennis Allen, "Systems and Methods for Delivering Sub-Threshold Therapy to a Patient", U.S. Appl. No. 61/801,917, filed Mar. 15, 2013.

"International Application Serial No. PCT/US2015/051339, International Preliminary Report on Patentability dated Apr. 6, 2017", 8 pgs.

"International Application Serial No. PCT/US2015/51339, International Search Report dated Nov. 27, 2015", 4 pgs.

"International Application Serial No. PCT/US2015/51339, Written Opinion dated Nov. 27, 2015", 6 pgs.

"Australian Application Serial No. 2015321559, First Examiners Report dated Sep. 28, 2017", 4 pgs.

"European Application Serial No. 15774820.3, Response filed Dec. 5, 2017 to Communication Pursuant to Rules 161(1) and 162 EPC dated May 31, 2017", 21 pgs.

"Japanese Application Serial No. 2017516060, Office Action dated Mar. 12, 2018", w/ English translation, 6 pgs.

"Australian Application Serial No. 2015321559, Response filed Mar. 26, 2018 to First Examiners Report dated Sep. 28, 2017", 13 pgs.

"Australian Application Serial No. 2015321559, Response filed Aug. 2, 2018 to Subsequent Examiners Report dated May 29, 2018", 17 pgs.

"Australian Application Serial No. 2015321559, Subsequent Examiners Report dated May 29, 2018", 7 pgs.

"Chinese Application Serial No. 201580051237.5, Office Action dated Aug. 30, 2018", w/ English translation, 20 pgs.

"Chinese Application Serial No. 201580051237.5, Response filed Jan. 11, 2019 to Office Action dated Aug. 30, 2018", w/ English claims, claims not amended, current claims in reference attachment, 8 pgs.

"Japanese Application Serial No. 2017-516060, Examiners Decision of Final Refusal dated Aug. 13, 2018", w/ English translation, 4 pgs.

"Japanese Application Serial No. 2017-516060, Response filed Dec. 13, 2018 to Examiners Decision of Final Refusal dated Aug. 13, 2018", w/ English claims, 12 pgs.

"Japanese Application Serial No. 2017516060, Response filed Jun. 11, 2018 to Office Action dated Mar. 12, 2018", w/ English claims, 8 pgs.

\* cited by examiner

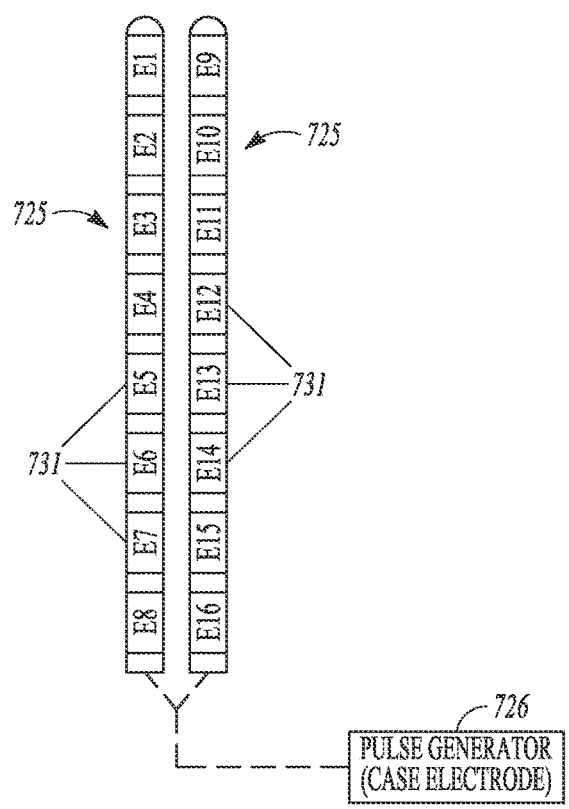
*FIG. 7*
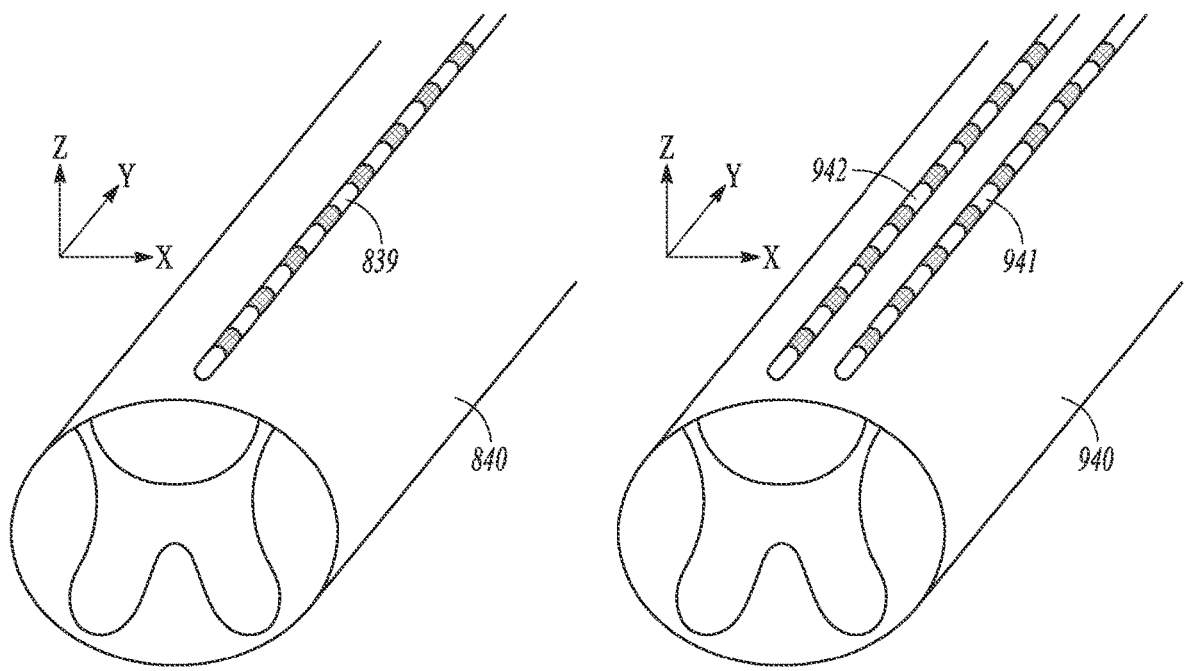
*FIG. 8*  *FIG. 9*

NEUROMODULATION SPECIFIC TO OBJECTIVE FUNCTION OF MODULATION FIELD FOR TARGETED TISSUE

CLAIM OF PRIORITY

This application claims the benefit of priority under 35 U.S.C. § 119(e) of U.S. Provisional Patent Application Ser. No. 62/054,081, filed on Sep. 23, 2014, which is herein incorporated by reference in its entirety.

TECHNICAL FIELD

This document relates generally to medical devices, and more particularly, to systems, devices and methods for delivering neural modulation.

BACKGROUND

Neural modulation has been proposed as a therapy for a number of conditions. Often, neural modulation and neural stimulation may be used interchangeably to describe excitatory stimulation that causes action potentials as well as inhibitory and other effects. Examples of neuromodulation include Spinal Cord Stimulation (SCS), Deep Brain Stimulation (DBS), Peripheral Nerve Stimulation (PNS), and Functional Electrical Stimulation (FES). SCS, by way of example and not limitation, has been used to treat chronic pain syndromes. Some neural targets may be complex structures with different types of nerve fibers. An example of such a complex structure is the neuronal elements in and around the spinal cord targeted by SCS.

SUMMARY

An example (e.g. "Example 1") of a system may include electrodes on at least one lead configured to be operationally positioned for use in modulating a volume of neural tissue, where the neural tissue has an activation function. The system may further include a neural modulation generator configured to deliver energy using at least some electrodes to generate a modulation field within the volume of neural tissue. The neural modulation generator may be configured to use a programmed modulation parameter set to generate the modulation field. The programmed modulation parameter set having values selected to control energy delivery using the at least some electrodes to achieve an objective function specific to the activation function of the volume of neural tissue to promote uniformity of a response to the modulation field in the volume of neural tissue along a span of the at least one lead. In Example 2, the subject matter of Example 1 may optionally be configured such that the volume of tissue includes a volume of dorsal horn tissue and the span of the at least one lead includes a span of at least three electrodes such that the objective function may promote uniformity of a response to the modulation field in the volume of dorsal horn tissue along the span of at least three electrodes and such that the neural modulation generator is configured to use the programmed modulation parameter set to generate a modulation field along the span of the at least three electrodes to promote uniformity of the response to the modulation field in the volume of dorsal horn tissue along the span of at least three electrodes.

In Example 3, the subject matter of any one or any combination of Examples 1-2 may optionally be configured such that the volume of neural tissue includes a volume of dorsal root tissue and the span of the at least one lead includes a span of at least three electrodes, and such that the objective function to promote uniformity of a response to the modulation field in the volume of dorsal root tissue along the span of at least three electrodes such that the neural modulation generator is configured to use the programmed modulation parameter set to generate a modulation field along the span of the at least three electrodes to promote uniformity of the response to the modulation field in the volume of dorsal root tissue along the span of at least three electrodes.

In Example 4, the subject matter of any one or any combination of Examples 1-3 may optionally be configured such that the objective function is a constant activation function.

In Example 5, the subject matter of any one or any combination of Examples 1-2 may optionally be configured such that the objective function is a constant E objective function to promote a constant electrical field in the volume of tissue or such that the objective function is a constant |E| objective function to promote a constant magnitude of an electrical field in the volume of tissue.

In Example 6, the subject matter of Example 1 may optionally be configured such that the volume of neural tissue includes a volume of dorsal column tissue and the span of the at least one lead includes a span of at least three electrodes, and such that the objective function promotes uniformity of a response to the modulation field in the volume of the dorsal column tissue along the span of at least three electrodes such that the neural modulation generator is configured to use the programmed modulation parameter set to generate a modulation field along the span of the at least three electrodes to promote uniformity of the response to the modulation field in the volume of dorsal column tissue along the span of at least three electrodes.

In Example 7, the subject matter of Example 6 may optionally be configured such that the objective function includes a constant voltage objective function to promote a constant voltage in the dorsal column.

In Example 8, the subject matter of Example 1 may optionally be configured such that the volume of tissue has an activation function for an electrical modulation parameter that is proportional to an n-order spatial derivative of the modulation field. The objective function for the modulation field includes a constant objective function for the n-order spatial derivative of the modulation field. The constant objective function promotes uniformity of a modulation response in the volume of tissue.

In Example 9, the subject matter of any one or any combination of Examples 1-8 may optionally be configured such that the electrical modulation parameter set includes fractionalization values for each electrode used to deliver the selected modulation field with the selected objective function.

In Example 10, the subject matter of any one or any combination of Examples 1-9 may optionally be configured such that the neural modulation generator and the electrodes are configured to cooperate to generate a sub-perception modulation field. The sub-perception modulation field may have an intensity below a patient-perception threshold, which is a boundary below which a patient does not sense generation of the modulation field.

In Example 11, the subject matter of Example 10 may optionally be configured such that the patient-perception threshold is a boundary below which the patient does not sense paresthesia such that the neural modulation generator and the electrodes are configured to cooperate to generate the sub-perception modulation field with an intensity below the boundary.

In Example 12, the subject matter of any one or any combination of Examples 1-11 may optionally be configured such that the system includes an implantable device and an external system. The implantable device may include the neural modulation generator. The external device may be configured to program the neural modulation generator.

In Example 13, the subject matter of Example 12 may optionally be configured such that the system includes a user interface configured to enable user selection of the objective function.

In Example 14, the subject matter of Example 13 may optionally be configured such that the user interface is configured to display a representation of the electrodes and the modulation field for the objective function.

In Example 15, the subject matter of any one or any combination of Examples 1-14 may optionally be configured such that the system is configured to determine fractionalization values for each active contact. The system may be configured to estimate a unit field for each active contact using an electric field model, where the estimated unit field is the field induced when the respective active contact is energized with an energy unit. The system may be further configured to determine weighted unit fields, including determine a perception threshold for each active electrode and calibrate the estimated unit field for each active electrode using the respective perception threshold, form constituent source(s) for the active contacts where each of the constituent sources includes an electrical contact to provide a source and another electrical contact to provide a sink, construct a transfer matrix using the weighted unit fields for the constituent sources, solve for contributions from each constituent sources to provide the selected modulation field, and compute fractionalization values for each active contact from the solution for the constituent sources.

An example (e.g. "Example 16") of a method for modulating a volume of tissue with an activation function may include selecting a modulation field to modulate the volume of tissue. Selecting the modulation field may include selecting an objective function for the modulation field that is specific to the volume of tissue and the activation function of the volume of tissue. The selected objective function for the modulation field may promote uniformity of a modulation response in the volume of tissue. The method may also modulate the volume of tissue using the selected modulation field with the selected objective function.

In Example 17, the subject matter of Example 16 may optionally be configured such that selecting the objective function for the modulation field may include selecting an objective function to modulate dorsal horn tissue.

In Example 18, the subject matter of Example 17 may optionally be configured such that selecting the objective function for the modulation field may include selecting a constant E objective function to modulate the dorsal horn tissue.

In Example 19, the subject matter of Example 17 may optionally be configured such that selecting the objective function for the modulation field may include selecting a constant |E| objective function to modulate the dorsal horn tissue.

In Example 20, the subject matter of Example 16 may optionally be configured such that selecting the objective function for the modulation field may include selecting an objective function to modulate dorsal column tissue.

In Example 21, the subject matter of Example 20 may optionally be configured such that selecting the objective function to stimulate dorsal column tissue may include selecting a constant activation function to modulate dorsal column tissue.

In Example 22, the subject matter of Example 21 may optionally be configured such that selecting the constant activation function to modulate dorsal column tissue may include selecting a constant voltage to modulate dorsal column tissue.

In Example 23, the subject matter of Example 16 may optionally be configured such that selecting the objective function for the modulation field includes selecting a dorsal horn objective function to modulate dorsal horn tissue, and selecting a dorsal column objective function to modulate dorsal column tissue.

In Example 24, the subject matter of Example 16 may optionally be configured such that the volume of tissue has an activation function for an electrical modulation parameter that is proportional to an n-order spatial derivative of the electrical modulation parameter, and selecting the objective function for the modulation field includes selecting a constant objective function for the n-order spatial derivative of the electrical modulation parameter, the selected constant objective function to promote uniformity of a modulation response in the volume of tissue.

In Example 25, the subject matter of any one or any combination of Examples 16-24 may optionally be configured such that the method may include determining fractionalization values for each active contact to provide the selected modulation field that meets the selected objective function. Modulating the volume of tissue using the selected modulation field with the selected objective function may include using the fractionalized values for each electrode used to deliver the selected modulation field with the selected objective function.

An example (e.g. "Example 26") of a method for modulating a volume of tissue with an activation function may include selecting a modulation field to modulate the volume of tissue. Selecting the modulation field may include selecting an objective function for the modulation field that is specific to the volume of tissue and the activation function of the volume of tissue. The selected objective function for the modulation field may promote uniformity of a modulation response in the volume of tissue. The method may also include determining fractionalization values for each active contact to provide the selected modulation field with the selected objective function, and modulating the volume of tissue using the selected modulation field with the selected objective function.

In Example 27, the subject matter of Example 26 may optionally be configured such that determining fractionalization values for each active contact includes estimating a unit field for each active contact using an electric field model, the estimated unit field being the field induced when the respective active contact is energized with an energy unit, determining weighted unit fields, including determining a perception threshold for each active electrode and calibrating the estimated unit field for each active electrode using the respective perception threshold, forming constituent source(s) for the active contacts, each of the constituent sources including an electrical contact to provide a source and another electrical contact to provide a sink, constructing a transfer matrix using the weighted unit fields for the constituent sources, solving for contributions from each constituent sources to provide the selected modulation field, and computing fractionalization values for each active contact from the solution for the constituent sources.

In Example 28, the subject matter of Example 27 may optionally be configured such that the method may include selecting active electrodes from a plurality of electrodes on at least one lead.

In Example 29, the subject matter of any one or any combination of Examples 16-28 may optionally be configured such that selecting the objective function for the modulation field may include selecting an objective function to modulate dorsal horn tissue. Selecting the objective function for the modulation field may include selecting a constant E objective function to modulate the dorsal horn tissue, or selecting a constant |E| objective function to modulate the dorsal horn tissue.

In Example 30, the subject matter of any one or any combination of Examples 16-28 may optionally be configured such that selecting the objective function for the modulation field may include selecting an objective function to modulate dorsal column tissue, and selecting a constant voltage to modulate dorsal column tissue.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 7 illustrates, by way of example, some features of the neuromodulation leads and a pulse generator.

FIG. 8 is a schematic view of a single electrical modulation lead implanted over approximately the longitudinal midline of the patient's spinal cord.

FIG. 9 illustrates an embodiment where an electrical modulation lead has been implanted more laterally with respect to the spinal cord, thereby placing it proximate the dorsal horn of the spinal cord, and the other electrical modulation lead has been implanted more medially with respect to the spinal cord, thereby placing it proximate the dorsal column of the spinal cord.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Figure 1:
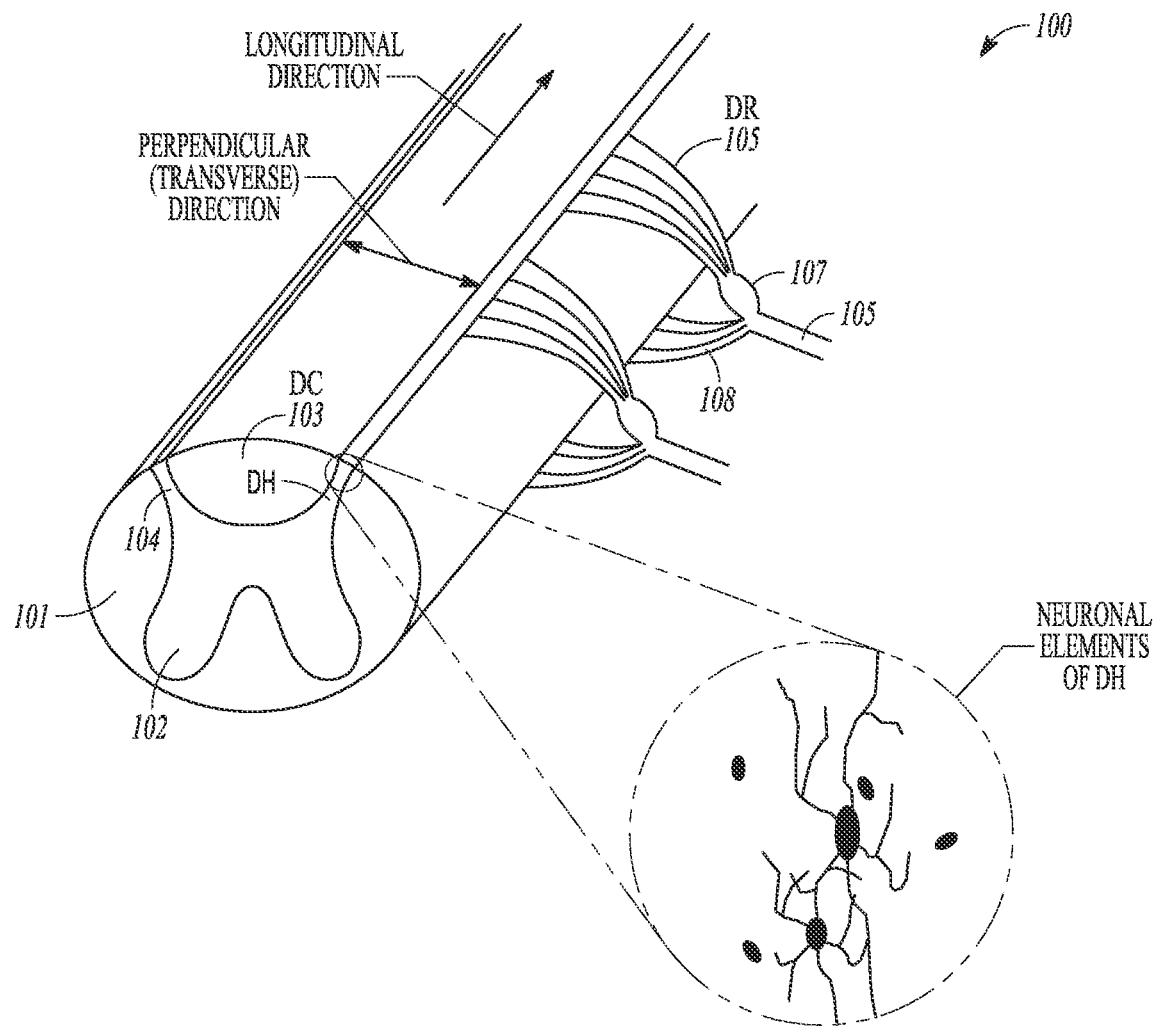
FIG. 1 illustrates a portion of a spinal cord.

Various embodiments described herein involve spinal cord modulation. A brief description of the physiology of the spinal cord is provided herein to assist the reader. FIG. 1 illustrates, by way of example, a portion of a spinal cord 100 including white matter 101 and gray matter 102 of the spinal cord. The gray matter 102 includes cell bodies, synapse, dendrites, and axon terminals. Thus, synapses are located in the gray matter. White matter 101 includes myelinated axons that connect gray matter areas. A typical transverse section of the spinal cord includes a central "butterfly" shaped central area of gray matter 102 substantially surrounded by an ellipse-shaped outer area of white matter 101. The white matter of the dorsal column (DC) 103 includes mostly large myelinated axons that form afferent fibers that run in an axial direction. The dorsal portions of the "butterfly" shaped central area of gray matter are referred to as dorsal horns (DH) 104. In contrast to the DC fibers that run in an axial direction, DH fibers can be oriented in many directions, including perpendicular to the longitudinal axis of the spinal cord. Examples of spinal nerves 105 are also illustrated, including a dorsal root (DR) 105, dorsal root ganglion 107 and ventral root 108. The dorsal root 105 mostly carries sensory signals into the spinal cord, and the ventral root functions as an efferent motor root. The dorsal and ventral roots join to form mixed spinal nerves 105.

SCS has been used to alleviate pain. A therapeutic goal for conventional SCS programming has been to maximize stimulation (i.e., recruitment) of the DC fibers that run in the white matter along the longitudinal axis of the spinal cord and minimal stimulation of other fibers that run perpendicular to the longitudinal axis of the spinal cord (dorsal root fibers, predominantly), as illustrated in FIG. 1. The white matter of the DC includes mostly large myelinated axons that form afferent fibers. While the full mechanisms of pain relief are not well understood, it is believed that the perception of pain signals is inhibited via the gate control theory of pain, which suggests that enhanced activity of innocuous touch or pressure afferents via electrical stimulation creates interneuronal activity within the DH of the spinal cord that releases inhibitory neurotransmitters (Gamma-Aminobutyric Acid (GABA), glycine), which in turn, reduces the hypersensitivity of wide dynamic range (WDR) sensory neurons to noxious afferent input of pain signals traveling from the dorsal root (DR) neural fibers that innervate the pain region of the patient, as well as treating general WDR ectopy. Consequently, the large sensory afferents of the DC nerve fibers have been targeted for stimulation at an amplitude that provides pain relief. Current implantable neuromodulation systems typically include electrodes implanted adjacent, i.e., resting near, or upon the dura, to the dorsal column of the spinal cord of the patient and along a longitudinal axis of the spinal cord of the patient.

Activation of large sensory DC nerve fibers also typically creates the paresthesia sensation that often accompanies conventional SCS therapy. Although alternative or artifactual sensations, such as paresthesia, are usually tolerated relative to the sensation of pain, patients sometimes report these sensations to be uncomfortable, and therefore, they can be considered an adverse side-effect to neuromodulation therapy in some cases. Some embodiments deliver sub-perception therapy that is therapeutically effective to treat pain, for example, but the patient does not sense the delivery of the modulation field (e.g. paresthesia). Sub-perception therapy may include higher frequency modulation (e.g. about 1500 Hz or above) of the spinal cord that effectively blocks the transmission of pain signals in the afferent fibers in the DC. Some embodiments herein selectively modulate DH tissue or DR tissue over DC tissue to provide sub-perception therapy. Such selective modulation is not delivered at these higher frequencies. For example, the selective modulation may be delivered at frequencies less than 1,200 Hz. The selective modulation may be delivered at frequencies less than 1,000 Hz in some embodiments. In some embodiments, the selective modulation may be delivered at frequencies less than 500 Hz. In some embodiments, the selective modulation may be delivered at frequencies less than 350 Hz. In some embodiments, the selective modulation may be delivered at frequencies less than 130 Hz. The selective modulation may be delivered at low frequencies (e.g. as low as 2 Hz). The selective modulation may be delivered even without pulses (e.g. 0 Hz) to modulate some neural tissue. By way of example and not limitation, the selective modulation may be delivered within a frequency range selected from the following frequency ranges: 2 Hz to 1,200 Hz; 2 Hz to 1,000 Hz, 2 Hz to 500 Hz; 2 Hz to 350 Hz; or 2 Hz to 130 Hz. Systems may be developed to raise the lower end of any these ranges from 2 Hz to other frequencies such as, by way of example and not limitation, 10 Hz, 20 Hz, 50 Hz or 100 Hz. By way of example and not limitation, it is further noted that the selective modulation may be delivered with a duty cycle, in which stimulation (e.g. a train of pulses) is delivered during a Stimulation ON portion of the duty cycle, and is not delivered during a Stimulation OFF portion of the duty cycle. By way of example and not limitation, the duty cycle may be about 10%±5%, 20%±5%, 30%±5%, 40%±5%, 50%±5% or 60%±5%. For example, a burst of pulses for 10 ms during a Stimulation ON portion followed by 15 ms without pulses corresponds to a 40% duty cycle.

Figure 2:
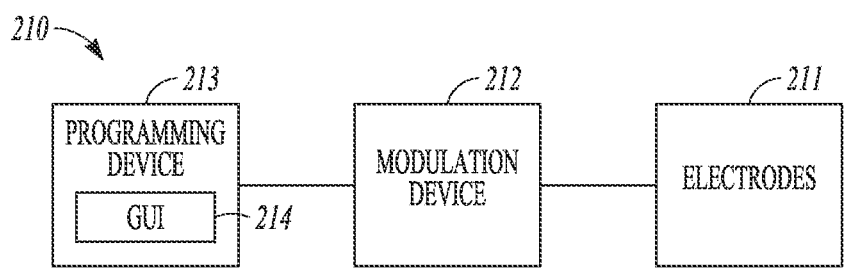
FIG. 2 illustrates, by way of example, an embodiment of a neuromodulation system.

FIG. 2 illustrates an embodiment of a neuromodulation system. The illustrated system 210 includes electrodes 211, a modulation device 212, and a programming device 213. The electrodes 211 are configured to be placed on or near one or more neural targets in a patient. The modulation device 212 is configured to be electrically connected to electrodes 211 and deliver neuromodulation energy, such as in the form of electrical pulses, to the one or more neural targets though electrodes 211. The delivery of the neuromodulation is controlled by using a plurality of modulation parameters, such as modulation parameters specifying the electrical pulses and a selection of electrodes through which each of the electrical pulses is delivered. In various embodiments, at least some parameters of the plurality of modulation parameters are programmable by a user, such as a physician or other caregiver. The programming device 213 provides the user with accessibility to the user-programmable parameters. In various embodiments, the programming device 213 is configured to be communicatively coupled to modulation device via a wired or wireless link. In various embodiments, the programming device 213 includes a graphical user interface (GUI) 214 that allows the user to set and/or adjust values of the user-programmable modulation parameters.

Figure 3:
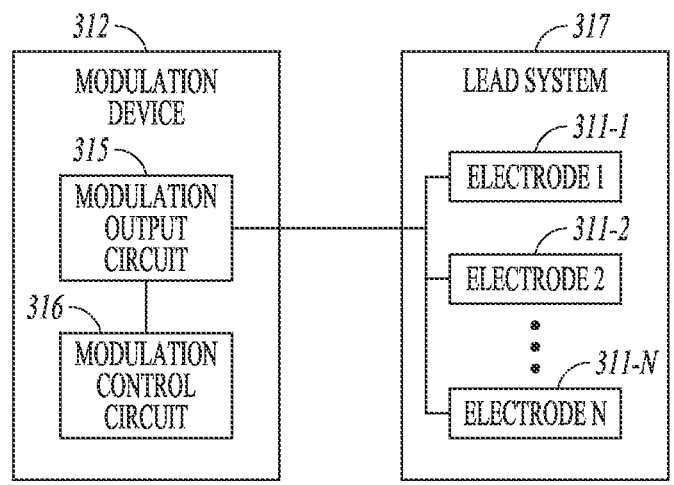
FIG. 3 illustrates, by way of example, an embodiment of a modulation device, such as may be implemented in the neuromodulation system of FIG. 2.

FIG. 3 illustrates an embodiment of a modulation device 312, such as may be implemented in the neuromodulation system 210 of FIG. 2. The illustrated embodiment of the modulation device 312 includes a modulation output circuit 315 and a modulation control circuit 316. Those of ordinary skill in the art will understand that the neuromodulation system 210 may include additional components such as sensing circuitry for patient monitoring and/or feedback control of the therapy, telemetry circuitry and power. The modulation output circuit 315 produces and delivers neuromodulation pulses. The modulation control circuit 316 controls the delivery of the neuromodulation pulses using the plurality of modulation parameters. The lead system 317 includes one or more leads each configured to be electrically connected to modulation device 312 and a plurality of electrodes 311-1 to 311-N distributed in an electrode arrangement using the one or more leads. Each lead may have an electrode array consisting of two or more electrodes, which also may be referred to as contacts. Multiple leads may provide multiple electrode arrays to provide the electrode arrangement. Each electrode is a single electrically conductive contact providing for an electrical interface between modulation output circuit 315 and tissue of the patient, where N≥2. The neuromodulation pulses are each delivered from the modulation output circuit 315 through a set of electrodes selected from the electrodes 311-1 to 311-N. The number of leads and the number of electrodes on each lead may depend on, for example, the distribution of target(s) of the neuromodulation and the need for controlling the distribution of electric field at each target. In one embodiment, by way of example and not limitation, the lead system includes two leads each having eight electrodes.

The neuromodulation system may be configured to modulate spinal target tissue or other neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, pulse width, and rate (or frequency) of the electrical pulses. Each electrode configuration, along with the electrical pulse parameters, can be referred to as a "modulation parameter set." Each set of modulation parameters, including fractionalized current distribution to the electrodes (as percentage cathodic current, percentage anodic current, or off), may be stored and combined into a modulation program that can then be used to modulate multiple regions within the patient.

The number of electrodes available combined with the ability to generate a variety of complex electrical pulses, presents a huge selection of modulation parameter sets to the clinician or patient. For example, if the neuromodulation system to be programmed has sixteen electrodes, millions of modulation parameter sets may be available for programming into the neuromodulation system. Furthermore, for example SCS systems may have thirty-two electrodes which exponentially increases the number of modulation parameters sets available for programming. To facilitate such selection, the clinician generally programs the modulation parameters sets through a computerized programming system to allow the optimum modulation parameters to be determined based on patient feedback or other means and to subsequently program the desired modulation parameter sets.

Conventional programming for SCS therapy uses paresthesia to select an appropriate modulation parameter set. The paresthesia induced by the modulation and perceived by the patient should be located in approximately the same place in the patient's body as the pain that is the target of treatment. When leads are implanted within the patient, an operating room (OR) mapping procedure may be performed to apply electrical modulation to test placement of the leads and/or electrodes, thereby assuring that the leads and/or electrodes are implanted in effective locations within the patient.

Once the leads are correctly positioned, a fitting procedure, which may be referred to as a navigation session, may be performed to program the external control device, and if applicable the neuromodulation device, with a set of modulation parameters that best addresses the painful site. Thus, the navigation session may be used to pinpoint the volume of activation (VOA) or areas correlating to the pain. The procedure may be implemented to target the tissue during implantation, or after implantation should the leads gradually or unexpectedly move that would otherwise relocate the modulation energy away from the target site. By reprogramming the neuromodulation device (typically by independently varying the modulation energy on the electrodes), the VOA can often be moved back to the effective pain site without having to re-operate on the patient in order to reposition the lead and its electrode array. When adjusting the VOA relative to the tissue, it is desirable to make small changes in the proportions of current, so that changes in the spatial recruitment of nerve fibers will be perceived by the patient as being smooth and continuous and to have incremental targeting capability.

Figure 4:
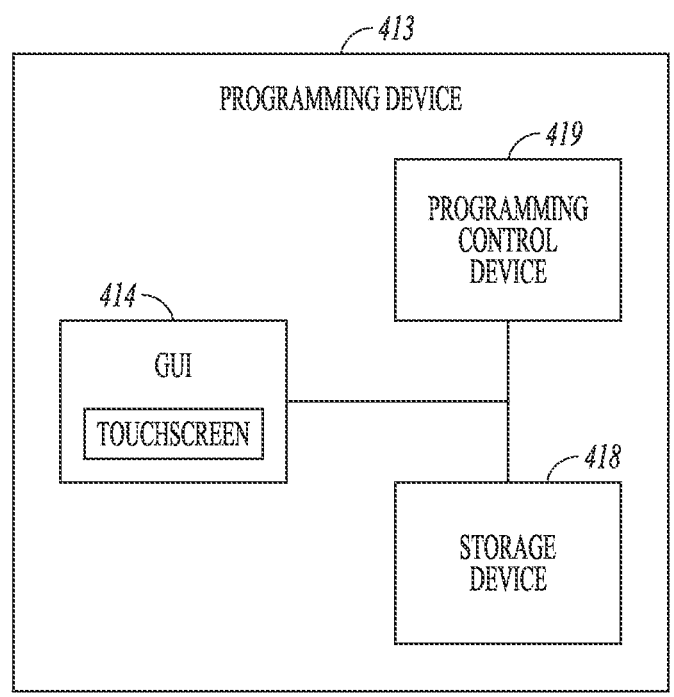
FIG. 4 illustrates, by way of example, an embodiment of a programming device, such as may be implemented as the programming device in the neuromodulation system of FIG. 2.

FIG. 4 illustrates an embodiment of a programming device 413, such as may be implemented as the programming device 213 in the neuromodulation system of FIG. 2. The programming device 413 includes a storage device 418, a programming control circuit 419, and a GUI 414. The programming control circuit 419 generates the plurality of modulation parameters that controls the delivery of the neuromodulation pulses according to the pattern of the neuromodulation pulses. In various embodiments, the GUI 414 includes any type of presentation device, such as interactive or non-interactive screens, and any type of user input devices that allow the user to program the modulation parameters, such as touchscreen, keyboard, keypad, touchpad, trackball, joystick, and mouse. The storage device 418 may store, among other things, modulation parameters to be programmed into the modulation device. The programming device 413 may transmit the plurality of modulation parameters to the modulation device. In some embodiments, the programming device 413 may transmit power to the modulation device. The programming control circuit 419 may generate the plurality of modulation parameters. In various embodiments, the programming control circuit 419 may check values of the plurality of modulation parameters against safety rules to limit these values within constraints of the safety rules.

In various embodiments, circuits of neuromodulation, including its various embodiments discussed in this document, may be implemented using a combination of hardware, software and firmware. For example, the circuit of GUI, modulation control circuit, and programming control circuit, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 5:
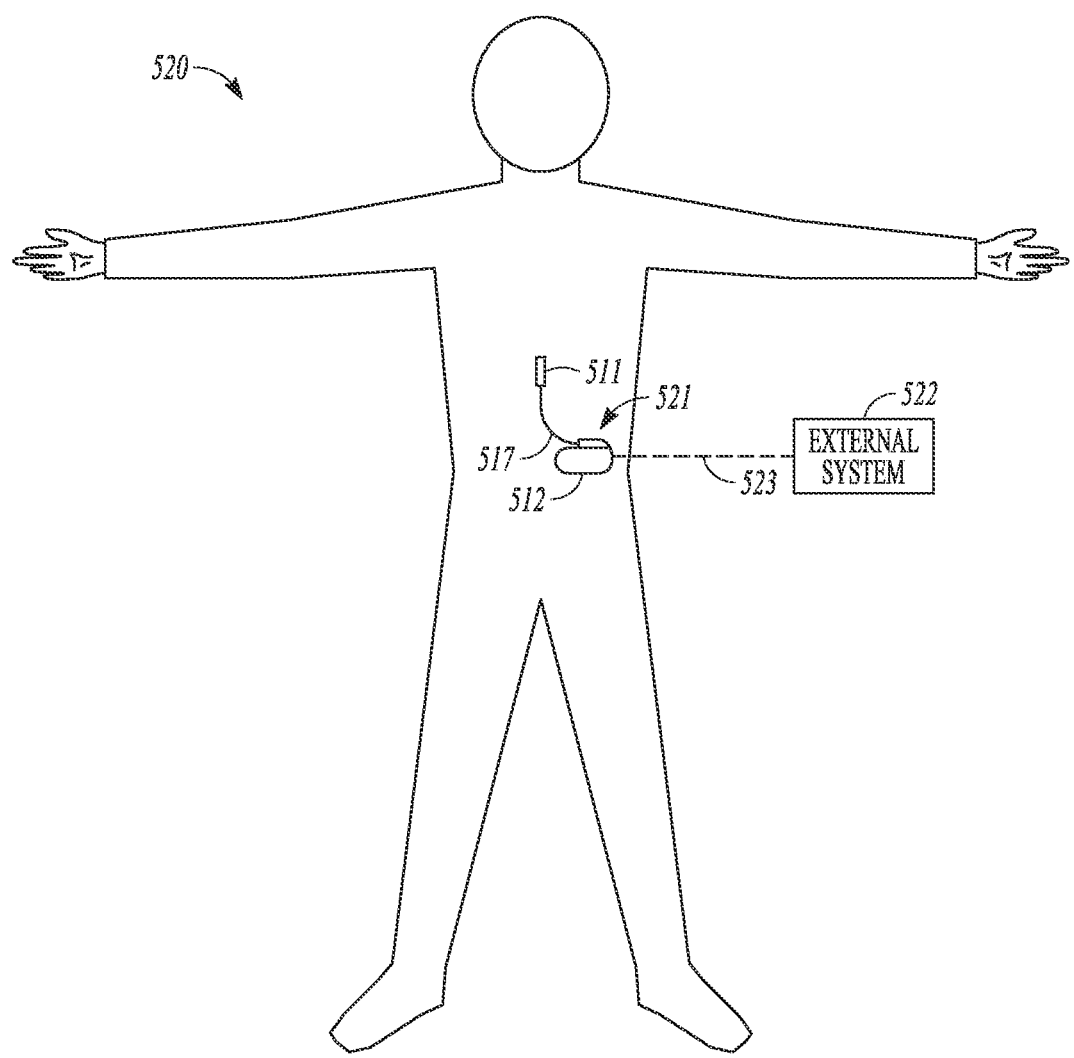
FIG. 5 illustrates, by way of example, an implantable neuromodulation system and portions of an environment in which system may be used.

FIG. 5 illustrates, by way of example, an implantable neuromodulation system and portions of an environment in which system may be used. The system is illustrated for implantation near the spinal cord. However, neuromodulation system may be configured to modulate other neural targets. The system 520 includes an implantable system 521, an external system 522, and a telemetry link 523 providing for wireless communication between implantable system 521 and external system 522. The implantable system is illustrated as being implanted in the patient's body. The implantable system 521 includes an implantable modulation device (also referred to as an implantable pulse generator, or IPG) 512, a lead system 517, and electrodes 511. The lead system 517 includes one or more leads each configured to be electrically connected to the modulation device 512 and a plurality of electrodes 511 distributed in the one or more leads. In various embodiments, the external system 402 includes one or more external (non-implantable) devices each allowing a user (e.g. a clinician or other caregiver and/or the patient) to communicate with the implantable system 521. In some embodiments, the external system 522 includes a programming device intended for a clinician or other caregiver to initialize and adjust settings for the implantable system 521 and a remote control device intended for use by the patient. For example, the remote control device may allow the patient to turn a therapy on and off and/or adjust certain patient-programmable parameters of the plurality of modulation parameters.

The neuromodulation lead(s) of the lead system 517 may be placed adjacent, i.e., resting near, or upon the dura, adjacent to the spinal cord area to be stimulated. For example, the neuromodulation lead(s) may be implanted along a longitudinal axis of the spinal cord of the patient. Due to the lack of space near the location where the neuromodulation lead(s) exit the spinal column, the implantable modulation device 512 may be implanted in a surgically-made pocket either in the abdomen or above the buttocks, or may be implanted in other locations of the patient's body. The lead extension(s) may be used to facilitate the implantation of the implantable modulation device 512 away from the exit point of the neuromodulation lead(s).

Figure 6:
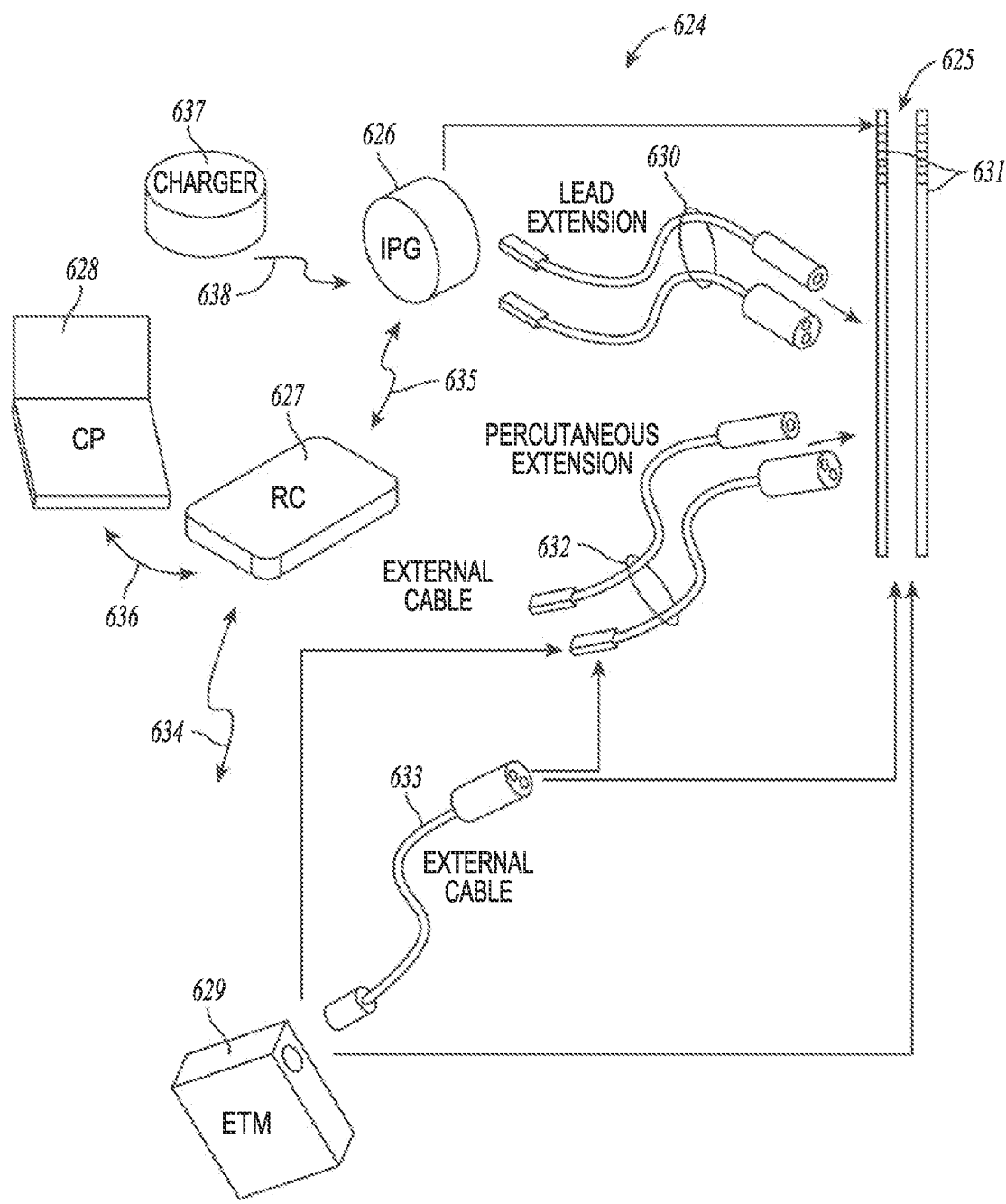
FIG. 6 illustrates, by way of example, an embodiment of a Spinal Cord Stimulation (SCS) system, which also may be referred to as a Spinal Cord Modulation (SCM) system.

FIG. 6 illustrates, by way of example, an embodiment of a SCS system, which also may be referred to as a Spinal Cord Modulation (SCM) system. The SCS system 624 may generally include a plurality (illustrated as two) of implantable neuromodulation leads 625, an implantable pulse generator (IPG) 626, an external remote controller RC 627, a clinician's programmer (CP) 628, and an external trial modulator (ETM) 629. The IPG 626 may be physically connected via one or more percutaneous lead extensions 630 to the neuromodulation leads 625, which carry a plurality of electrodes 631. As illustrated, the neuromodulation leads 625 may be percutaneous leads with the electrodes arranged in-line along the neuromodulation leads. Any suitable number of neuromodulation leads can be provided, including only one, as long as the number of electrodes is greater than two (including the IPG case function as a case electrode) to allow for lateral steering of the current. Alternatively, a surgical paddle lead can be used in place of one or more of the percutaneous leads. The IPG 626 includes pulse generation circuitry that delivers electrical modulation energy in the form of a pulsed electrical waveform (i.e., a temporal series of electrical pulses) to the electrodes in accordance with a set of modulation parameters.

The ETM 629 may also be physically connected via the percutaneous lead extensions 632 and external cable 633 to the neuromodulation leads 625. The ETM 629 may have similar pulse generation circuitry as the IPG 626 to deliver electrical modulation energy to the electrodes accordance with a set of modulation parameters. The ETM 629 is a non-implantable device that is used on a trial basis after the neuromodulation leads 625 have been implanted and prior to implantation of the IPG 626, to test the responsiveness of the modulation that is to be provided. Functions described herein with respect to the IPG 626 can likewise be performed with respect to the ETM 629.

The RC 627 may be used to telemetrically control the ETM 629 via a bi-directional RF communications link 634. The RC 627 may be used to telemetrically control the IPG 626 via a bi-directional RF communications link 635. Such control allows the IPG 626 to be turned on or off and to be programmed with different modulation parameter sets. The IPG 626 may also be operated to modify the programmed modulation parameters to actively control the characteristics of the electrical modulation energy output by the IPG 626. A clinician may use the CP 628 to program modulation parameters into the IPG 626 and ETM 629 in the operating room and in follow-up sessions.

The CP 628 may indirectly communicate with the IPG 626 or ETM 629, through the RC 627, via an IR communications link 636 or other link. The CP 628 may directly communicate with the IPG 626 or ETM 629 via an RF communications link or other link (not shown). The clinician detailed modulation parameters provided by the CP 628 may also be used to program the RC 627, so that the modulation parameters can be subsequently modified by operation of the RC 627 in a stand-alone mode (i.e., without the assistance of the CP 628). Various devices may function as the CP 628. Such devices may include portable devices such as a lap-top personal computer, mini-computer, personal digital assistant (PDA), tablets, phones, or a remote control (RC) with expanded functionality. Thus, the programming methodologies can be performed by executing software instructions contained within the CP 628. Alternatively, such programming methodologies can be performed using firmware or hardware. In any event, the CP 628 may actively control the characteristics of the electrical modulation generated by the IPG 626 to allow the desired parameters to be determined based on patient feedback or other feedback and for subsequently programming the IPG 626 with the desired modulation parameters. To allow the user to perform these functions, the CP 628 may include a user input device (e.g., a mouse and a keyboard), and a programming display screen housed in a case. In addition to, or in lieu of, the mouse, other directional programming devices may be used, such as a trackball, touchpad, joystick, touch screens or directional keys included as part of the keys associated with the keyboard. An external device (e.g. CP) may be programmed to provide display screen(s) that allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical modulation energy output by the neuromodulation leads, and select and program the IPG with modulation parameters in both a surgical setting and a clinical setting.

An external charger 637 may be a portable device used to transcutaneously charge the IPG via a wireless link such as an inductive link 638. Once the IPG has been programmed, and its power source has been charged by the external charger or otherwise replenished, the IPG may function as programmed without the RC or CP being present.

FIG. 7 illustrates, by way of example, some features of the neuromodulation leads 725 and a pulse generator 726. The pulse generator 726 may be an implantable device (IPG) or may be an external device such as may be used to test the electrodes during an implantation procedure. In the illustrated example, one of the neuromodulation leads has eight electrodes (labeled E1-E8), and the other neuromodulation lead has eight electrodes (labeled E9-E16). The actual number and shape of leads and electrodes may vary for the intended application. An implantable pulse generator (IPG) may include an outer case for housing the electronic and other components. The outer case may be composed of an electrically conductive, biocompatible material, such as titanium, that forms a hermetically-sealed compartment wherein the internal electronics are protected from the body tissue and fluids. In some cases, the outer case may serve as an electrode (e.g. case electrode). The IPG may include electronic components, such as a controller/processor (e.g., a microcontroller), memory, a battery, telemetry circuitry, monitoring circuitry, modulation output circuitry, and other suitable components known to those skilled in the art. The microcontroller executes a suitable program stored in memory, for directing and controlling the neuromodulation performed by IPG. Electrical modulation energy is provided to the electrodes in accordance with a set of modulation parameters programmed into the pulse generator. The electrical modulation energy may be in the form of a pulsed electrical waveform. Such modulation parameters may comprise electrode combinations, which define the electrodes that are activated as anodes (positive), cathodes (negative), and turned off (zero), percentage of modulation energy assigned to each electrode (fractionalized electrode configurations), and electrical pulse parameters, which define the pulse amplitude (measured in milliamps or volts depending on whether the pulse generator supplies constant current or constant voltage to the electrode array), pulse width (measured in microseconds), pulse rate (measured in pulses per second), and burst rate (measured as the modulation on duration X and modulation off duration Y). Electrodes that are selected to transmit or receive electrical energy are referred to herein as "activated," while electrodes that are not selected to transmit or receive electrical energy are referred to herein as "non-activated."

Electrical modulation occurs between or among a plurality of activated electrodes, one of which may be the IPG case. The system may be capable of transmitting modulation energy to the tissue in a monopolar or multipolar (e.g., bipolar, tripolar, etc.) fashion. Monopolar modulation occurs when a selected one of the lead electrodes is activated along with the case of the IPG, so that modulation energy is transmitted between the selected electrode and case. Any of the electrodes E1-E16 and the case electrode may be assigned to up to k possible groups or timing "channels." In one embodiment, k may equal four. The timing channel identifies which electrodes are selected to synchronously source or sink current to create an electric field in the tissue to be stimulated. Amplitudes and polarities of electrodes on a channel may vary. In particular, the electrodes can be selected to be positive (anode, sourcing current), negative (cathode, sinking current), or off (no current) polarity in any of the k timing channels. The IPG may be operated in a mode to deliver electrical modulation energy that is therapeutically effective and causes the patient to perceive delivery of the energy (e.g. therapeutically effective to relieve pain with perceived paresthesia), and may be operated in a sub-perception mode to deliver electrical modulation energy that is therapeutically effective and does not cause the patient to perceive delivery of the energy (e.g. therapeutically effective to relieve pain without perceived paresthesia).

The IPG may be configured to individually control the magnitude of electrical current flowing through each of the electrodes. For example, a current generator may be configured to selectively generate individual current-regulated amplitudes from independent current sources for each electrode. In some embodiments, the pulse generator may have voltage regulated outputs. While individually programmable electrode amplitudes are desirable to achieve fine control, a single output source switched across electrodes may also be used, although with less fine control in programming. Neuromodulators may be designed with mixed current and voltage regulated devices.

FIGS. 8-11 illustrate, by way of example, a difference in electrical field strength in the longitudinal and transverse directions when the current is fractionalized such that the electrical field in the longitudinal direction generated by the fractionalized current delivered to each electrode is approximately equal. The voltage at a patient's spinal cord (especially at the DC fibers) is approximately equal in the longitudinal direction, resulting in a voltage gradient of approximately zero along the DC. This may require different amounts of fractionalized current delivered to each electrode. Calibration techniques are used to determine the proper current fractionalization. With the current fractionalized to a plurality of electrodes on the electrical modulation lead, the resulting field can be calculated by superimposing the fields generated by the current delivered to each electrode. Moreover each electrical field has a longitudinal component and a transverse component.

FIG. 8 is a schematic view of a single electrical modulation lead 839 implanted over approximately the longitudinal midline of the patient's spinal cord 840. It is understood that additional leads or lead paddle(s) may be used, such as may be used to provide a wider electrode arrangement and/or to provide the electrodes closer to dorsal horn elements, and that these electrode arrays also may implement fractionalized current. FIG. 9 illustrates an embodiment where an electrical modulation lead 941 has been implanted more laterally with respect to the spinal cord, thereby placing it proximate the dorsal horn of the spinal cord, and the other electrical modulation lead 942 has been implanted more medially with respect to the spinal cord, thereby placing it proximate the dorsal column of the spinal cord 940. Placement of the lead more proximate to the DH than the DC may be desirable to preferentially stimulate DH elements over DC neural elements for a sub-perception therapy. Any other plurality of leads or a multiple column paddle lead can also be used. Longitudinal component of the electrical field is directed along the y-axis depicted in FIG.

8, and a transverse component of the electrical field is directed along the x-axis depicted in FIG. 8.

Figure 10:
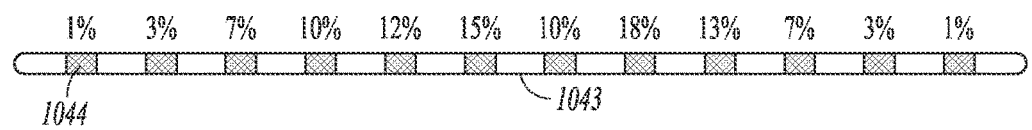
FIG. 10 illustrates a schematic view of the electrical modulation lead showing an example of the fractionalization of the anodic current delivered to the electrodes on the electrical modulation lead.

FIG. 10 is a schematic view of the electrical modulation lead 1043 showing an example of the fractionalization of the anodic current delivered to the electrodes on the electrical modulation lead. These figures illustrate fractionalization using monopolar modulation where a case electrode of the IPG is the only cathode, and carries 100% of the cathodic current. The fractionalization of the anodic current shown in FIG. 10 does not deliver an equal amount of current to each electrode 1044, because this embodiment takes into account electrode/tissue coupling differences, which are the differences in how the tissue underlying each electrode reacts to electrical modulation. Also, the ends of the portion of the electrical modulation lead include electrodes having lower gradient in the longitudinal direction. The magnitude of the electrical field tapers down at the ends of the electrical modulation lead. Fractionalization of the current to the electrodes is controlled such that the tissue underlying each electrode in the middle portion of the electrical modulation lead reacts approximately equally to the electrical modulation, or tissue activation underlying each electrode are eliminated. However, the resulting fractionalization is not equal. In the embodiment shown in FIG. 10, fractionalization of the current to the middle electrodes varies from 10% to 18%, reflecting the variation in the tissue underlying those electrodes. The fractionalization across the electrical modulation lead can vary in any manner as long as the total of fractionalized currents equals 100%. Various embodiments described herein implement a programmed algorithm to determine the appropriate fractionalization to achieve a desired modulation field property (e.g. constant electric field, or constant electric field magnitude, or constant voltage).

Figure 11:
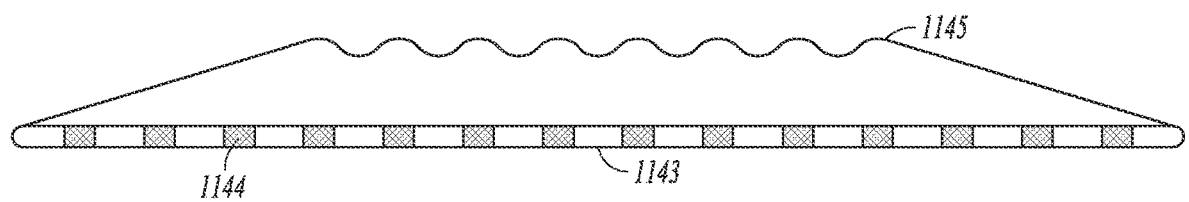
FIG. 11 illustrates, by way of example, a schematic illustration of a gradient in the longitudinal direction along the axis of the electrical modulation lead.

FIG. 11 illustrates, by way of example, a schematic illustration of a gradient in the longitudinal direction along the axis of the electrical modulation lead. The electrical field strength 1145 in the longitudinal direction is plotted over a schematic representation of the electrodes 1144 on the electrical modulation lead 1143. The illustration in FIG. 11 shows that the electrical field strength is substantially constant over the middle portion of the electrical modulation lead, but may form a wave with very small amplitude because of the gaps between the electrodes in the lead. This substantially constant electrical field forms a small longitudinal gradient, which minimizes activation of the large myelinated axons in the dorsal column. The illustration in FIG. 11 also shows the electrical field in the longitudinal direction tapering at the ends of the electrical modulation lead.

Figure 12:
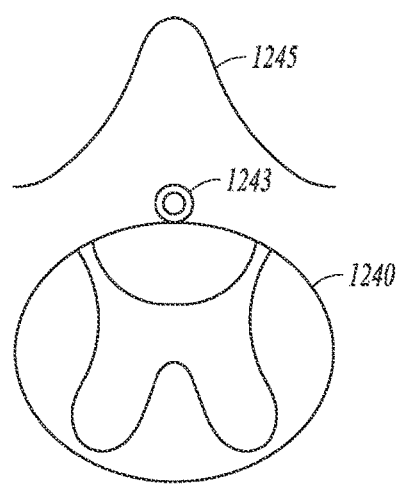
FIG. 12 illustrates, by way of example, a schematic illustration of a gradient in the transverse direction.
Figure 13A:
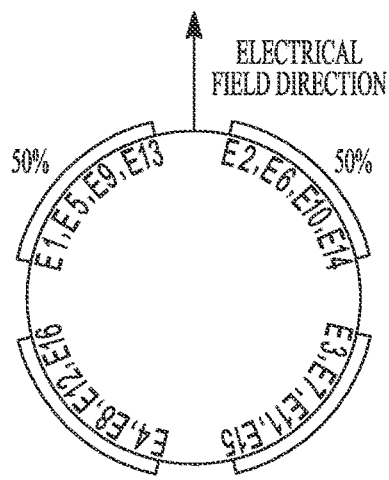
FIGS. 13A-13C and 14A-14C illustrate, by way of example, neural modulation leads in which the electrodes may take the form of segmented electrodes that are circumferentially and axially disposed about the neuromodulation leads.
Figure 13B:
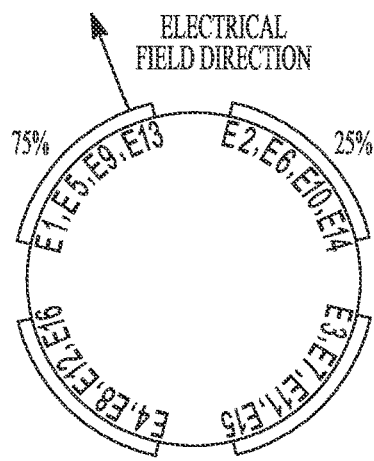
Figure 13C:
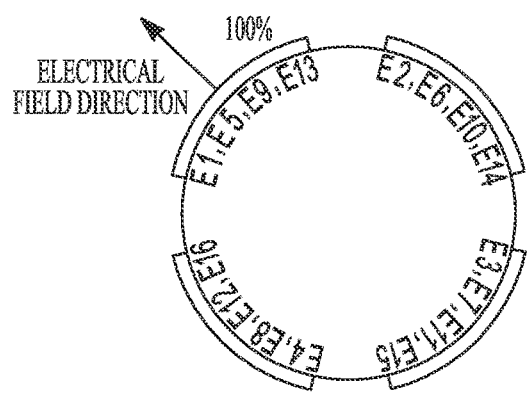
Figure 14A:
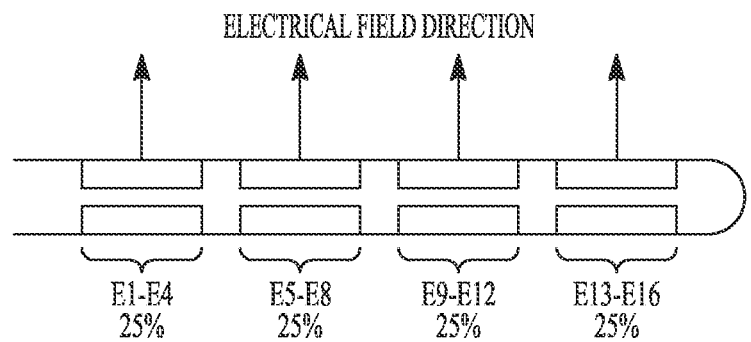
Figure 14B:
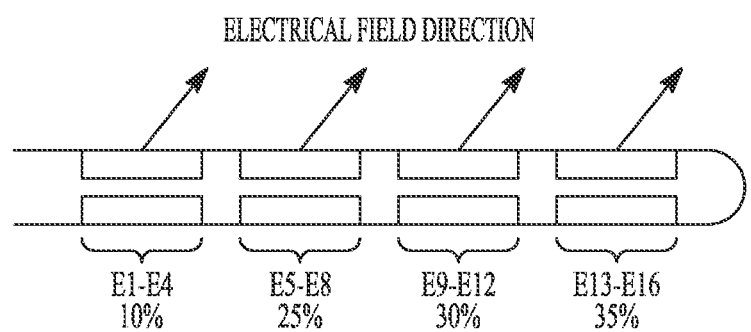
Figure 14C:
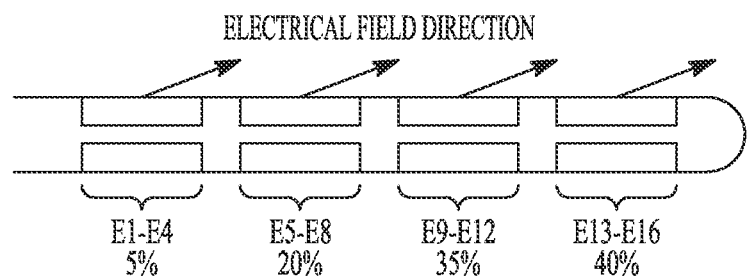

FIG. 12 illustrates, by way of example, a schematic illustration of a gradient in the transverse direction. The transverse electrical field strength 1245 in the transverse direction is plotted over a schematic representation of the electrical modulation lead 1243 and the spinal cord 1240 of the patient. The illustration in FIG. 12 shows that the transverse electrical field strength is greatest adjacent the electrical modulation lead and falls off lateral of the electrical modulation lead. Use of additional modulation leads to widen the electrode array may be used to provide desired fractionalization to also provide a region of a substantially constant electric field for a distance along the transverse direction. Substantially constant electric fields favor modulation of dorsal horn and/or dorsal root neuronal elements over dorsal column neuronal elements.

FIGS. 13A-13C and 14A-14C illustrate, by way of example, neural modulation leads in which the electrodes may take the form of segmented electrodes that are circumferentially and axially disposed about the neuromodulation leads. By way of non-limiting example, each neuromodulation lead may carry sixteen electrodes, arranged as four rings of electrodes (the first ring consisting of electrodes E1-E4; the second ring consisting of electrodes E5-E8; the third ring consisting of electrodes E9-E12; and the fourth ring consisting of electrodes E13-E16) or four axial columns of electrodes (the first column consisting of electrodes E1, E5, E9, and E13; the second column consisting of electrodes E2, E6, E10, and E14; the third column consisting of electrodes E3, E7, E11, and E15; and the fourth column consisting of electrodes E4, E8, E12, and E16). The actual number and shape of leads and electrodes may vary according to the intended application.

The SCS system may be used to deliver electrical energy to the spinal cord of the patient using electrical fields having different orientations, also as generally illustrated in FIGS. 13A-13C and 14A-14C. The orientation of the electrical field may be selected to target the different directions/orientations of the DH elements. To generate electrical fields in different medio-lateral directions, the electrodes may have different current fractionalizations in the radial direction. Although it is desirable that the electrical fields preferentially stimulate DH and/or DR elements over the DC elements, as discussed above, the electrical fields may still be oriented in different rostro-caudal directions (i.e., the direction of the electrical fields as projected on a longitudinal plane through the spinal cord), although preferably not in an orientation that will result in the perception of paresthesia. To generate electrical fields in different rostro-caudal directions, the electrodes may have different current fractionalizations in the longitudinal direction.

The SCS system may be configured to deliver different electrical fields to achieve a temporal summation of modulation in the DH elements. The electrical fields can be generated respectively on a pulse-by-pulse basis. For example, a first electrical field can be generated by the electrodes (using a first current fractionalization) during a first electrical pulse of the pulsed waveform, a second different electrical field can be generated by the electrodes (using a second different current fractionalization) during a second electrical pulse of the pulsed waveform, a third different electrical field can be generated by the electrodes (using a third different current fractionalization) during a third electrical pulse of the pulsed waveform, a fourth different electrical field can be generated by the electrodes (using a fourth different current fractionalized) during a fourth electrical pulse of the pulsed waveform, and so forth. These electrical fields may be rotated or cycled through multiple times under a timing scheme, where each field is implemented using a timing channel. The electrical fields may be generated at a continuous pulse rate, or may be bursted on and off. Furthermore, the interpulse interval (i.e., the time between adjacent pulses), pulse amplitude, and pulse duration during the electrical field cycles may be uniform or may vary within the electrical field cycle.

An embodiment modifies the fractionalized current delivered to each electrode to minimize the electrical field gradient in the longitudinal direction, so as to minimize activation of the DC elements Minimizing activation of the DC elements can include a model-based calculation, where the model includes the information from the calibration. A discrete activating function can be calculated by the formula: $AF(n) = G_a/(\pi \times d \times l) \times [V_e(n-1) - 2 V_e(n) + V_e(n+1)]$, wherein $G_a$ is the axonal intermodal conductance, d is the axonal diameter, l is the length of the node of Ranvier, $V_e(n)$ is the strength of the electric field at the node for which the activating function is determined, $V_e(n-1)$ is the strength of the electric field at the node preceding the node for which the activating function is determined, and $V_e(n+1)$ is the strength of the electric field at the node following the node for which the activating function is determined. Using this formula, the discrete activating function is calculated from the conductance normalized to the surface area of the node of Ranvier.

Modulation thresholds vary from patient to patient and from electrode to electrode within a patient. An electrode/tissue coupling calibration of the electrodes may be performed to account for these different modulation thresholds and provide a more accurate fractionalization of the current between electrodes. For example, perception threshold may be used to normalize the electrodes. The RC or the CP may be configured to prompt the patient to actuate a control element, once paresthesia is perceived by the patient. In response to this user input, the RC or the CP may be configured to respond to this user input by storing the modulation signal strength of the electrical pulse train delivered when the control element is actuated. Other sensed parameter or patient-perceived modulation values (e.g. constant paresthesia, or maximum tolerable paresthesia) may be used to provide the electrode/tissue coupling calibration of the electrodes. These sensed parameter or patient-perceived modulation values may be used to estimate the current fractionalization by minimizing the sum of the square of the discrete activating function divided by the determined value (e.g. perception threshold) at each electrode on an electrical modulation lead. Squaring the discrete activating function, or any driving force from the electrical field, eliminates the differences in depolarizing and hyperpolarizing fields. The current fractionalization that results in a minimize sum minimizes the field gradient in the longitudinal direction.

The remainder of this document discusses various embodiments that relate to enhancing the effectiveness a modulation field such as a sub-perception modulation field, various embodiments that relate to the electrode selection and refinement for use in delivering a modulation field such as a sub-perception field, and various embodiments relate to the calibration of sub-perception modulation. These embodiments may be implemented separately, or may be implemented in various combination(s). Such combination(s) may be useful for delivering sub-perception modulation of the DH or DR tissue over DC tissue. However, some embodiments may be used to deliver other modulation therapies.

Enhanced Modulation Field

Neural tissue in the region of the spinal cord has different characteristics. For example, DC fibers (mostly myelinated axons) run in an axial direction, whereas DH (e.g. neuronal cell terminals, neuronal cell bodies, dendrites, and axons) fibers are oriented in many directions. The distance from typically-placed epidural SCS leads to DH fibers are different than the distance from these leads to DC fibers. Further, DH fibers and dorsal column fibers have different responses (e.g. activation functions) to electrical modulation. The strength of modulation (i.e., depolarizing or hyperpolarizing) of the DC fibers and neurons is described by the so-called "activation function" which is proportional to the second-order spatial derivative of the voltage along the longitudinal axis of the spine ($\partial^2 V/\partial x^2$). This is partially because the large myelinated axons in DC are primarily aligned longitudinally along the spine. On the other hand, the likelihood of generating action potentials in DH fibers and neurons is described by an activating function that is proportion to the first-order spatial derivative of the voltage along the spine ($\partial V/\partial x$), which is otherwise known as the electric field. Thus, the DH activating function is proportional to the first-order derivative of the voltage along the fiber axis, whereas the DC activating function is proportional to the second-order derivative of the voltage along the fiber axis. Accordingly, the distance from the electrical field locus affects the DH activating function ($\partial V/\partial x$) less than it affects the dorsal column activating function $\partial^2 V/\partial x^2$. The neuronal elements (e.g., neurons, dendrites, axons, cell bodies, and neuronal cell terminals) in the DH can be preferentially stimulated over the DC neuronal elements by minimizing the longitudinal gradient of an electrical field generated by a neuromodulation lead along the DC, thereby providing therapy in the form of pain relief without creating the sensation of paresthesia. This technique relies, at least partially on the natural phenomenon that DH fibers and DC fibers have different responses (activation functions) to electrical modulation.

Various embodiments for enhancing modulation field selectively modulate DH and/or DR tissue over DC tissue. Conventional SCS activates DC fiber axons, and the orthodromic propagation of action potentials induces perception of paresthesia in the brain and antidromic propagation of action potentials to fiber collaterals and terminals ending in DH evokes pain control mechanism in DH. Various embodiments shape the stimulation field to preferably stimulate fiber terminals ending in DH and/or DR to provide pain relief without inducing paresthesia. For example, uniformity in a first order gradient of voltage (i.e. uniformity in electric field) may be more efficient in stimulating DH fiber terminals and/or stimulating DR fibers. Uniformity across a larger field may eliminate the needs for searching optimal stimulation site and create broader coverage of pain. For example, the uniformity may extend between or among two or more electrodes within an arrangement of electrodes. In other examples, the uniformity may extend among three, four, five, six or more electrodes within an arrangement of electrodes to eliminate the needs for searching for an optimal simulation site and creating a broader therapeutic coverage. Thus, the uniformity extends over a substantial portion of the lead. Some embodiments are configured to determine a modulation parameter set to create a field shape to provide a broad and uniform modulation field to enhance modulation of targeted neural tissue (e.g. DH tissue or DR tissue). Some embodiments are configured to determine a modulation parameter set to create a field shape to reduce or minimize modulation of non-targeted tissue (e.g. DC tissue). Various embodiments disclosed herein are directed to shaping the modulation field to enhance modulation of some neural structures and diminish modulation at other neural structures. The modulation field may be shaped by using multiple independent current control (MICC) or multiple independent voltage control to guide the estimate of current fractionalization among multiple electrodes and estimate a total amplitude that provide a desired strength. For example, the modulation field may be shaped to enhance the modulation of DH neural tissue and to minimize the modulation of DC tissue. A benefit of MICC is that MICC accounts for various in electrode-tissue coupling efficiency and perception threshold at each individual contact, so that "hot-spot" stimulation is eliminated.

The modulation field may be shaped to provide a constant electric field (E) at the DH tissue in a selected direction. The electric field (E) at the DH in any direction is the negative gradient (negative rate of change) of the scalar potential field (V) in that direction. Due to the linearity of field superposition, a transfer function can be formed to estimate the EDH(x,y,z) at selected direction induced by unit current from a single electrode located at (x0, y0, z0), the total E field is the linear combination of the E field induced by currents from each active electrode weighted by the current fractionalization. In an example, the modulation field may be a constant V field along the DC tissue.

Due to the linearity of field superposition, a transfer function can be formed to estimate the VDC(x,y,z) at selected direction induced by unit current from a single electrode located at (x0, y0, z0), the total V field is the linear combination of the V field induced by currents from each active electrode weighted by the current fractionalization.

Various embodiments predict the amplitude. For example, the target V magnitude at DC or the target E magnitude at DH may be determined as a percentage of perception threshold of current (Ith) under certain modulation configuration (monopole, bipole or tripole, etc). For example, a set of V magnitude at selected locations of DH can be estimated as Vtarget using mathematical model under the monopolar Ith (or under the desired percentage of Ith) from a selected electrode. When current is fractionalized among more than one electrode, the total amplitude can be estimated as the one that would maximally approximate the Vtarget from the combination of current fractionalization. An empirical method may estimate the Ith under the desired fractionalization and adjust the amplitude down.

Figure 15:
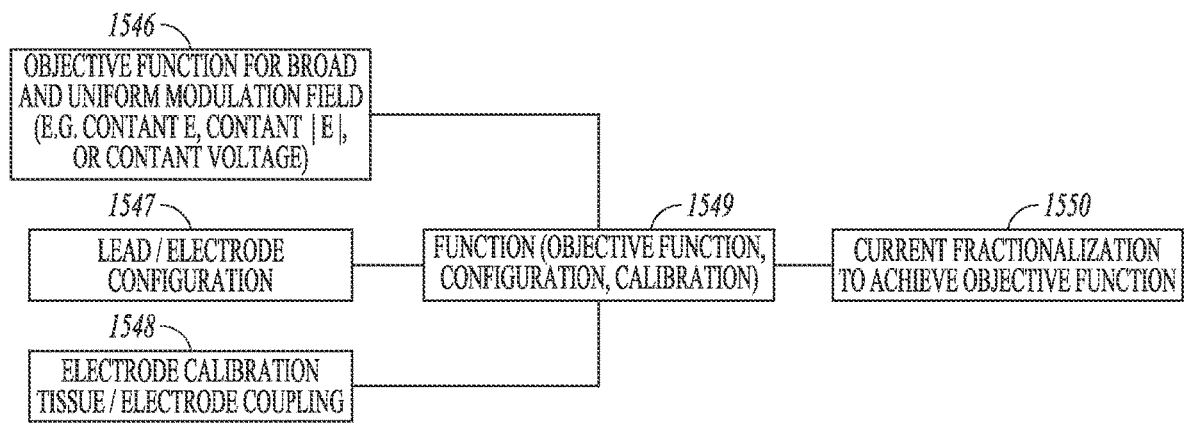
FIG. 15 illustrates, by way of example, an embodiment for determining fractionalization to achieve a target function.

FIG. 15 illustrates, by way of example, an embodiment for determining fractionalization to achieve an objective function. An objective function refers to a function with desirable characteristics for modulating the targeted tissue. The objective function may also be referred to as an objective target function. An objective function 1546 for a broad and uniform modulation field is identified for a given volume of tissue. Examples of an objective function includes a constant E (electric field), a constant |E| (electric field magnitude), and a constant voltage. The lead and electrode configuration 1547 are also identified, as well as calibration for electrode tissue coupling 1548. A function 1549 is performed that is dependent on the objective function, the lead and electrode configuration and the calibration. The result of the function is the fractionalization of modulation energy (e.g. current) 1550 for each electrode to achieve the objective function.

Figure 16:
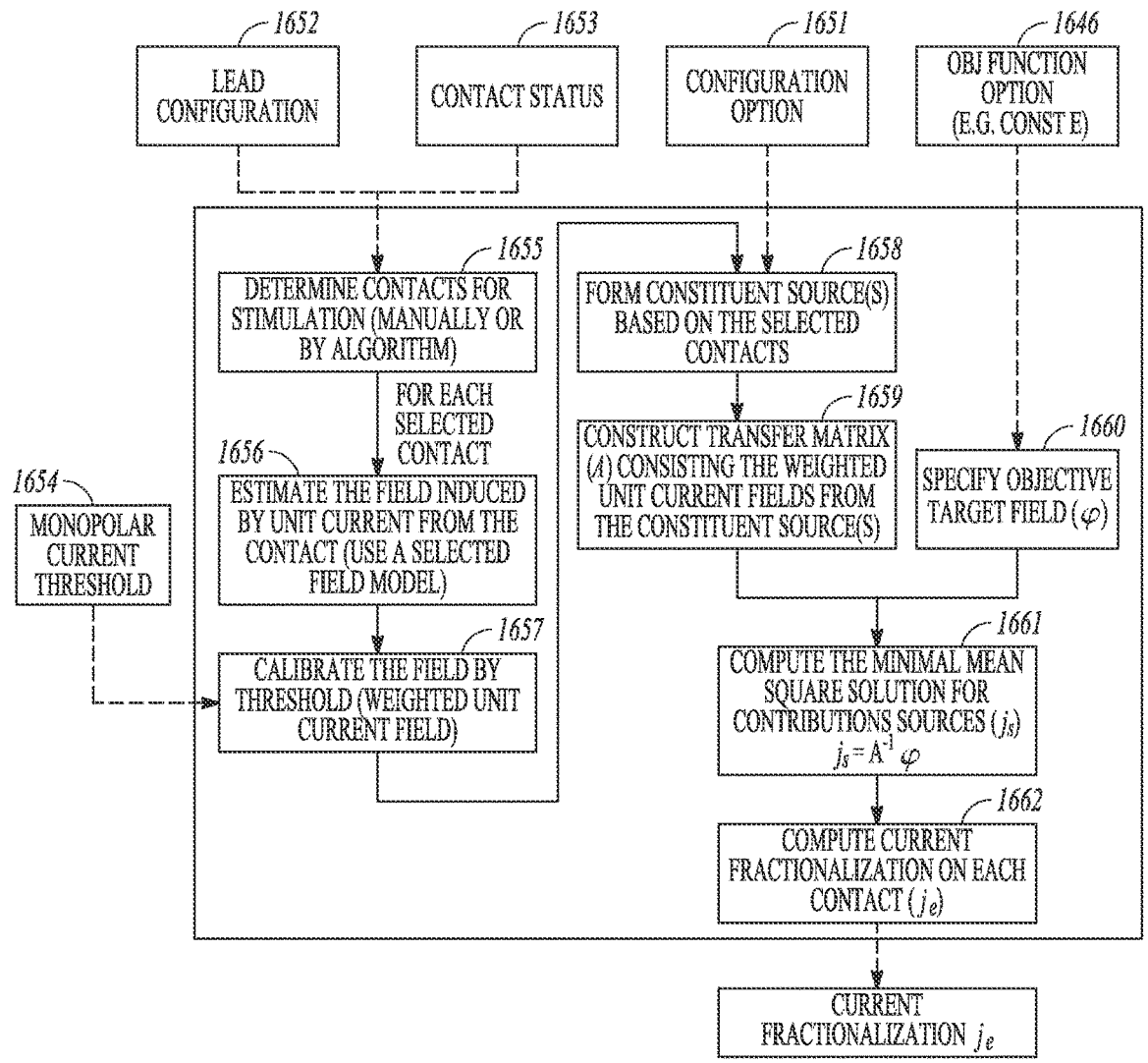
FIG. 16 illustrates, by way of example, an embodiment for determining fractionalization to achieve a target function with more detail.

FIG. 16 illustrates, by way of example, an embodiment for determining fractionalization to achieve an objective function with more detail. An objective target function 1646 (e.g. constant E) is provided as an input to a process. Other inputs to the process include a configuration option 1651, a lead configuration 1652 and electrode contact status 1653, and a threshold 1654 such as a current threshold or more particularly a monopolar current threshold. The lead configuration 1652 and contact status 1653 identify an electrode arrangement, identifying a position of each electrode to determine the field. The overall field is a superimposed field from each electrode. The configuration option 1651 refers to monopolar (same polarity for all activated electrodes) and multipolar options (combined anode and cathodes in field). The threshold is used to compensate for electrode/tissue coupling differences.

The contacts for stimulation may be determined automatically or manually 1655 from the lead configuration and contact status. A selected field model may be used to estimate the field induced by unit current from the contact 1656. The field is calibrated using the threshold 1657. For example, the unit current field may be weighted. Constituent forces are formed based on the selected contacts 1658, and a transfer matrix 1659 is constructed to use to compute the minimal mean square solution using contributions from the constituent sources 1661 and using a specified target field 1660. The solution can be used to compute the current fractionalization on each contact 1662.

Figure 17:
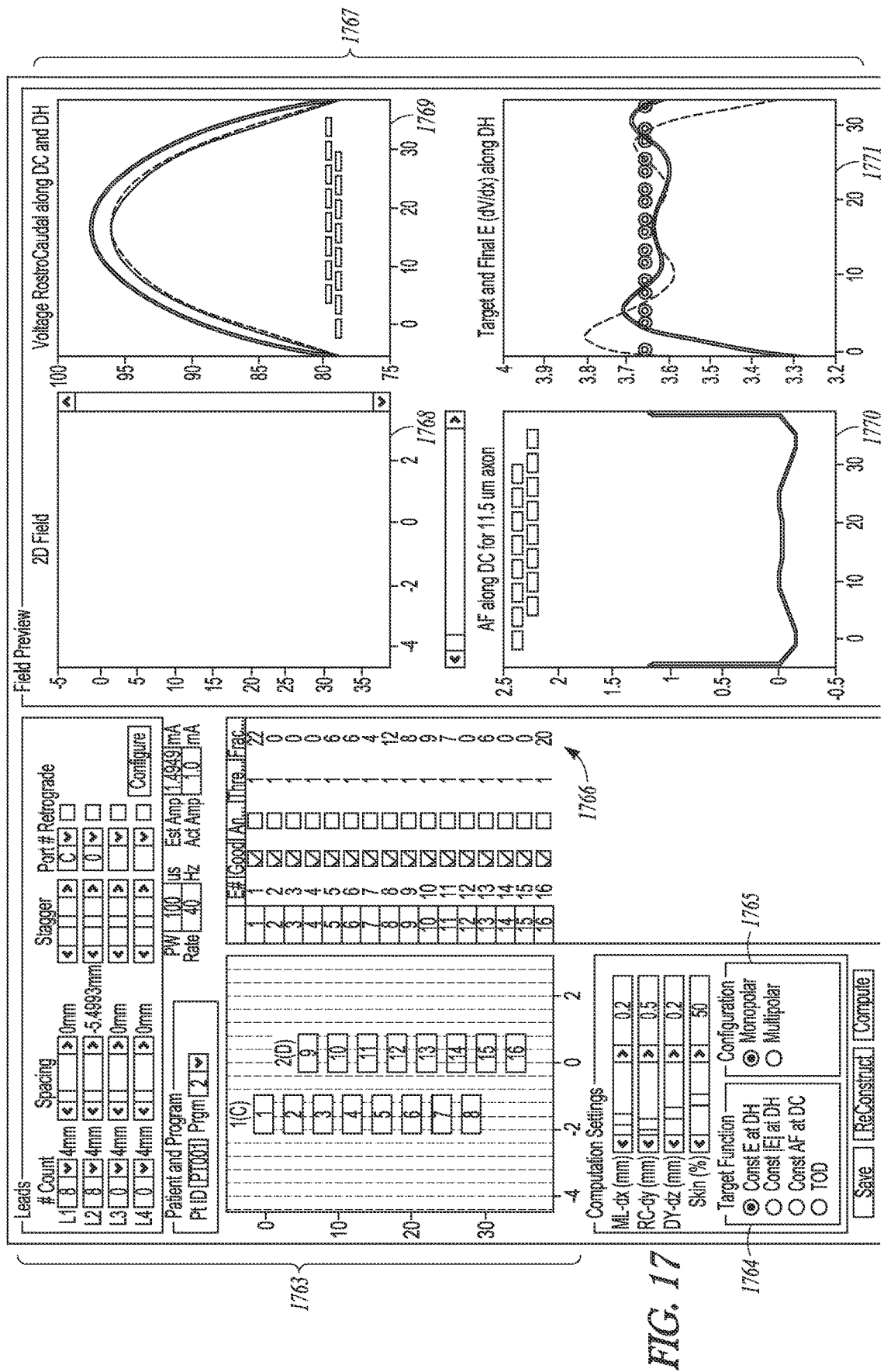
FIG. 17 illustrates, by way of example, a programming interface that may be provided in a GUI of a CP or other external device.
Figure 18:
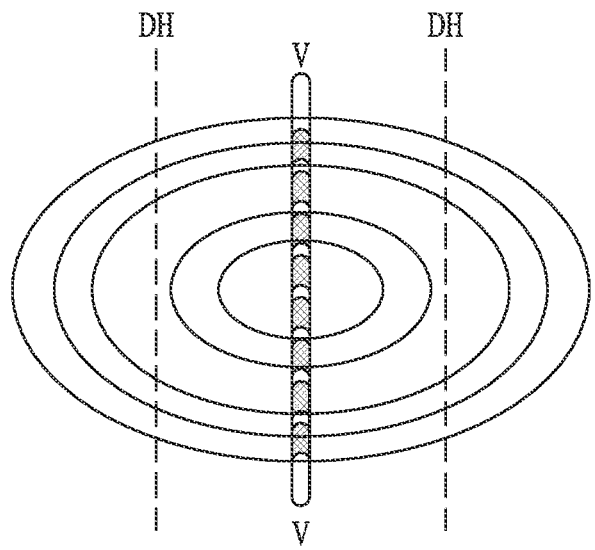
FIG. 18 illustrates, by way of example, equipotential voltage lines for a lead, along with a representation of the lead and the dorsal horns.
Figure 19:
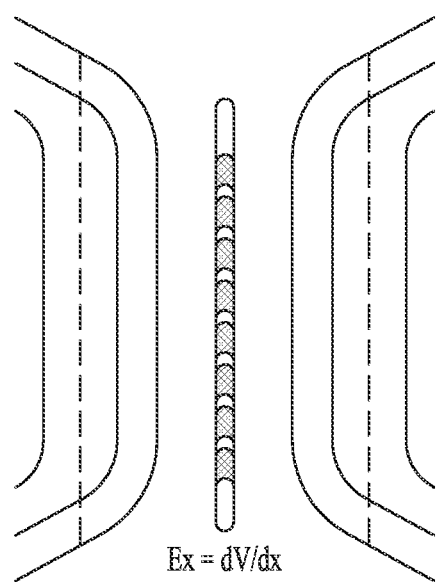
FIGS. 19-20 illustrate, by way of example, a substantial uniform electric field along with a representation of the lead and the dorsal horns.
Figure 20:
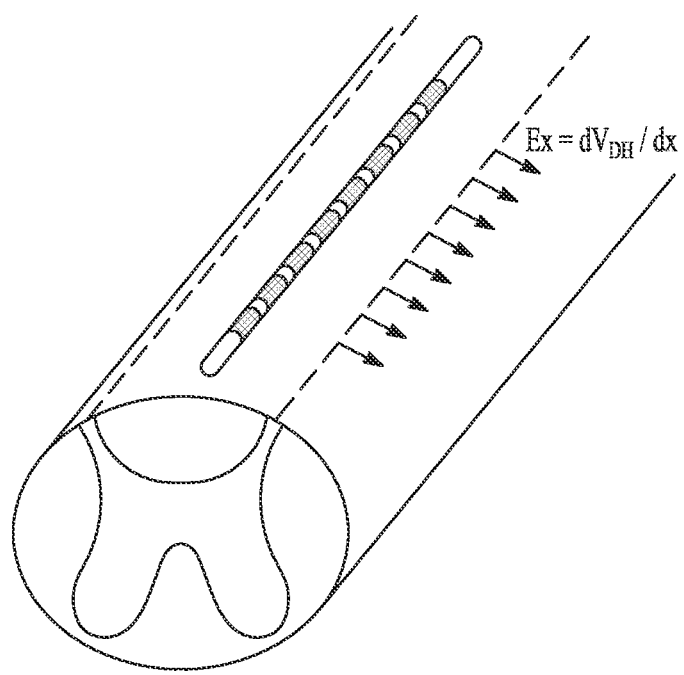

FIG. 17 illustrates, by way of example, a programming interface that may be provided in a GUI of a CP or other external device. The interface may be used to identify, among other things, the electrode arrangement 1763. Furthermore, as generally illustrated at the bottom left portion of the screen, the interface may be used to identify the target function specific for a volume of tissue (e.g. Constant E at DH, Constant |E| at DH, or constant activation function AF or constant voltage at DC) 1764 and the electrode configuration (e.g. monopolar or multipolar) 1765. The fractionalized current for the electrodes to provide the objective target function may be identified such as is shown at 1766. Furthermore, the interface may provide a visual representation of the target and final target function 1767, along with a representation of the relative position of the field (e.g. electrode contacts). For example, the visual representations may include a representation of a two dimensional field 1768, a representation of a voltage rostrocaudal along DC and DH 1769, an Activation Function (AF) along DC 1770, and a target and final E field (dV)/dx along DH 1771. For example, the AF along DC is very low along a substantial portion of the electrode arrangement, thus indicating that the afferent fibers in the DC are not being modulated by the modulation field. However, the E field in the transverse direction (X direction) is uniform along DH for a substantial portion of the electrode arrangement, thus indicating that the field is substantially uniform in modulating DH and/or DR neuronal tissue along a substantial portion of the electrode arrangement. FIG. 18 illustrates, by way of example, equipotential voltage lines (such as plotted in 1769) for a lead, along with a representation of the lead and the dorsal horns; and FIGS. 19-20 illustrate, by way of example, a substantial uniform electric field (such as plotted in 1771), along with a representation of the lead and the dorsal horns.

Various embodiments provide a method for modulating a volume of tissue with an activation function, where the method includes selecting a modulation field to modulate the volume of tissue, including selecting an objective function for the modulation field that is specific to the volume of tissue and the activation function of the volume of tissue. The objective function for the modulation field promotes uniformity of a modulation response in the volume of tissue. The volume of tissue may be modulated using the selected modulation field with the selected objective function. The objective function may be an objective function to modulate DH tissue and/or DR tissue. Examples of such an objective function include a constant E objective function or a constant |E| objective function. The objective function may be a constant activation function. The objective function may be an objective function to modulate DC tissue. Examples of such an objective function include a constant activation function, such a constant voltage, to discourage action potentials within the dorsal column tissue. The selected objective function may include both a DH objective function and a DC objective function. According to some embodiments, the volume of tissue has an activation function for an electrical modulation parameter that is proportional to an n-order spatial derivative of the electrical modulation parameter. The objective function for the modulation field may be selected to provide a constant objective function for the n-order spatial derivative of the electrical modulation parameter to promote uniformity of a modulation response in the volume of tissue. Fractionalization values for each activated contact may be determined to provide the selected modulation field with the selected objective function. Modulating the volume of tissue using the selected modulation field with the selected objective function includes using the fractionalized values for each electrode used to deliver the selected modulation field with the selected objective function.

Various embodiments provide a method for modulating a volume of tissue with an activation function. The method may comprise selecting a modulation field to modulate the volume of tissue, wherein selecting the modulation field includes selecting an objective function for the modulation field that is specific to the volume of tissue and the activation function of the volume of tissue. The selected objective function for the modulation field promotes uniformity of a modulation response in the volume of tissue. Fractionalization values are determined for each active contact to provide the selected modulation field with the selected objective function. The volume of tissue may be modulated using the selected modulation field with the selected objective function. The fractionalization values for each active contact maybe determined by estimating a unit field for each active contact using an electric field model, the estimated unit field being the field induced when the respective active contact is energized with an energy unit, determining weighted unit fields, including determining a perception threshold for each active electrode and calibrating the estimated unit field for each active electrode using the respective perception threshold, forming constituent source(s) for the active contacts, each of the constituent sources including an electrical contact to provide a source and another electrical contact to provide a sink, constructing a transfer matrix using the weighted unit fields for the constituent sources, solving for contributions from each constituent sources to provide the selected modulation field, and computing fractionalization values for each active contact from the solution for the constituent sources. Active electrodes may be selected from a plurality of electrodes on at least one lead.

A system may be used to implement any of these methods. An example of such a system include electrodes on at least one lead configured to be operationally positioned for use in modulating a volume of neural tissue and a neural modulation generator configured to use at least some electrodes to generate a modulation field within the volume of tissue. The neural tissue has an activation function. The activation function represents a response the neural tissue has to the modulation field. The neural modulation generator is configured to deliver energy using a programmed modulation parameter set to generate the modulation field within the volume of neural tissue along the at least one lead. The programmed modulation parameter set has values selected to control energy delivery to achieve an objective function specific to the activation function of the volume of neural tissue to promote uniformity of a response to the modulation field in the volume of neural tissue along a span of the at least one lead. The system may include an implantable device and an external system where the implantable device includes with the neural modulation generator. The external device may be configured to program the neural modulation generator. The external device may include a user interface configured to enable user selection of the objective function. The user interface may also display a representation of the electrodes and the modulation field for the objective function.

Various embodiments enhance the modulation of DH tissue or nerve root tissue using spatial and temporal techniques. DH tissue is described below as an example. Preferential engagement of DH tissue may facilitate pain relieve without the need for modulation-induced sensation. The spatial technique provides DH modulation with a constant field (e.g. approximately constant electric field in volume of DH tissue). For example, electrodes are selected, and electrode polarities and strengths can be designed to be approximately constant in the superficial DH (e.g., Rexed's laminae I-III or IV) along the full electrode or the portion(s) of the array deemed important for therapy. Axon terminals in the DH are believed to be one of the most excitable and possibly the most excitable neural element in the vicinity of the electric field. The temporal technique provides DH in bursts to enhance the effectiveness of exciting axon terminals in the DH. Data in cat spinal cord ventral horn suggest that consecutive pulses close in time are particularly effective as exciting terminals, and showed this with a burst of 4 pulses that decreased the threshold by ~4× (intra-burst frequency of about 500 Hz; Gustaffson et al., 1976). Pulse delivery at continuous high rate (equal to or greater than a few hundred Hz) may also effectively excite the terminals, but a burst is expected to be efficient.

Figure 21:
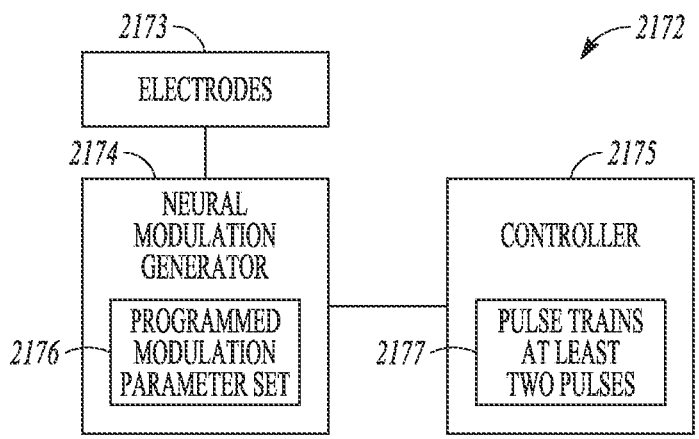
FIG. 21 illustrates, by way of example, a system configured to preferentially engage dorsal horn (DH) neuronal tissue.

FIG. 21 illustrates, by way of example, a system configured to preferentially engage DH tissue. The illustrated system 2172 includes electrodes 2173, a neural modulation generator 2174, and a controller 2175. The neural stimulation generator 2174 is configured to use a programmed modulation parameter set 2176 to preferentially modulate DH tissue over DC tissue. For example, as discussed above, the programmed modulation parameter set may be configured to promote uniformity of the modulation field in the DH tissue. The modulation field is a vector and depends on the selective orientation. The modulation may be configured to promote uniformity in more than one orientation. A segmented lead, by way of example, may be used to promote uniformity in more than one orientation. For example, the programmed modulation parameter set may be configured to provide a constant E field or a constant |E| field to preferentially engage DH tissue. The controller 2175 may be used to deliver a pulse train 2177 for the programmed modulation parameter set. The pulse train includes at least two pulses may also be referred to as a burst of pulses. These bursts are believed to enhance the excitation of terminals in the DH, and thus can be used to further increase the selectivity of modulating the DH tissue over the DC tissue.

Figure 22:
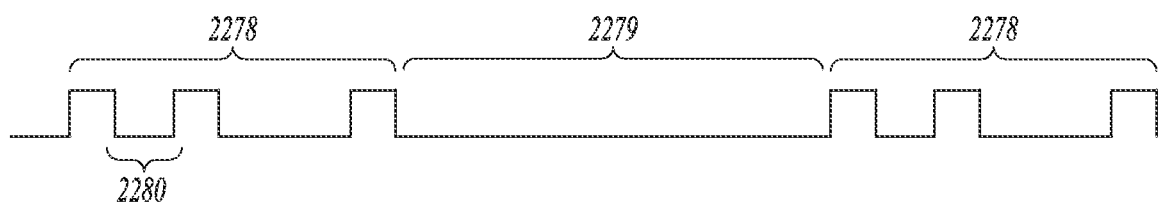
FIG. 22 generally illustrates, by way of example, a pulse train.

FIG. 22 generally illustrates, by way of example, a pulse train. According to some embodiments, the duration 2278 of each pulse train is less than 100 ms. For example, in some embodiments, the duration 2278 of each pulse train is more than 2 ms and less than 50 ms. The time 2279 between successive pulse trains may be more than the duration 2278 of each of the successive pulse trains. Each pulse train may be less than 10 pulses. The interpulse duration 2280 of the pulse trains may be within a range of 2 ms to 5 ms.

As the neuronal elements in the DH have variant spatial distribution, orientation, alignments and variant temporal responses in the neural activity, a single fixed modulation paradigm may not optimized to maximize the therapeutic effect. Various embodiments are provided to create varying and patterned modulation field. For example, various embodiments may vary the lead geometry used to deliver the modulation, using directional leads to vary the radial direction of current delivery, and therefore varying the V and E field distribution along the DH (see, for example, FIGS. 13A-13C and 14A-14C along with the corresponding description. Various embodiments may use a patterned modulation train). The patterned stimulation train may include various patterns of pulse and various pulse shapes (e.g. rectangular, sinusoidal, etc.). Various embodiments use a spatial pattern. For example, the modulation may alternate between two or among three or more sets of modulation electrodes. In another example, multiple fields may be used to change the spatial pattern of modulation. Various embodiments use a temporal pattern. For example, some embodiments implement multiple channels that are out of phase with each other (i.e. non-synchronous) to provide the pattern of the modulation. Some embodiments interleave multiple channel modulation, where the channels have at least one different modulation parameter value for a parameter such as amplitude, pulse width, repeat rate, or burst pattern. Thus, the modulation parameter value (e.g. amplitude, pulse width, repeat rate, or burst pattern) may be changed by switching between two channels or among more than three channels. Some embodiments modulate the pulses in the modulation. For example, one or more of the amplitude, rate or pulse width may be modulated to provide a temporal variation in the pattern. Some embodiments modify the pulse train in manner to mimic a natural response of the human body. Various embodiments vary both the spatial and temporal pattern.

Electrode Span Selection and Refinement

Sub-perception modulation can pose some challenges for selecting and refining the electrodes for use to deliver the modulation. For example, conventional SCS may simply try to provide a small targeted stimulation to modulate the DC and cause paresthesia. The modulation for conventional SCS can be adjusted to map the paresthesia over the region of pain. However, a patient does not perceive the delivery of the modulation energy for sub-perception modulation.

The programming algorithm for sub-perception modulation may pre-select all available contacts along the rostra-caudal direction as cathodes (or anodes) to deliver DH modulation. However, a consequence of a such a wide span selection is higher power requirements with probably an excess of modulation being delivered. It is desirable to decrease power requirements without compromising therapy outcomes using an algorithm to select a customized, smaller rostra-caudal span.

Various embodiments start with full-lead then use a search algorithm to reduce the span and improve energy efficiency. This can be done from the RC or CP, or in the IPG with RC feedback. The proposed algorithms may rely on some form of feedback indicating the effectiveness of the modulation. For example, a patient may provide feedback regarding pain relief. Feedback may also provide a biomarker signal.

The system may include a feature to confirm that the modulation along the full lead is effective and then focus the modulation along a portion of the lead. Thus, for example, a generally uniform modulation field may be provided along this smaller portion of the lead. This field is still broad as it may be provided across an area with multiple electrode contacts, but it is less than the entire electrode arrangement using electrode array(s) on the lead(s).

Various embodiments may provide a rostra-caudal focus feature that includes a binary search feature. The binary search feature segments the lead or array of electrodes from a full set of electrodes into at least two subsets of electrodes that defines partial lead search regions. The binary search feature may confirm that modulation along the full lead is effective.

Figure 23:
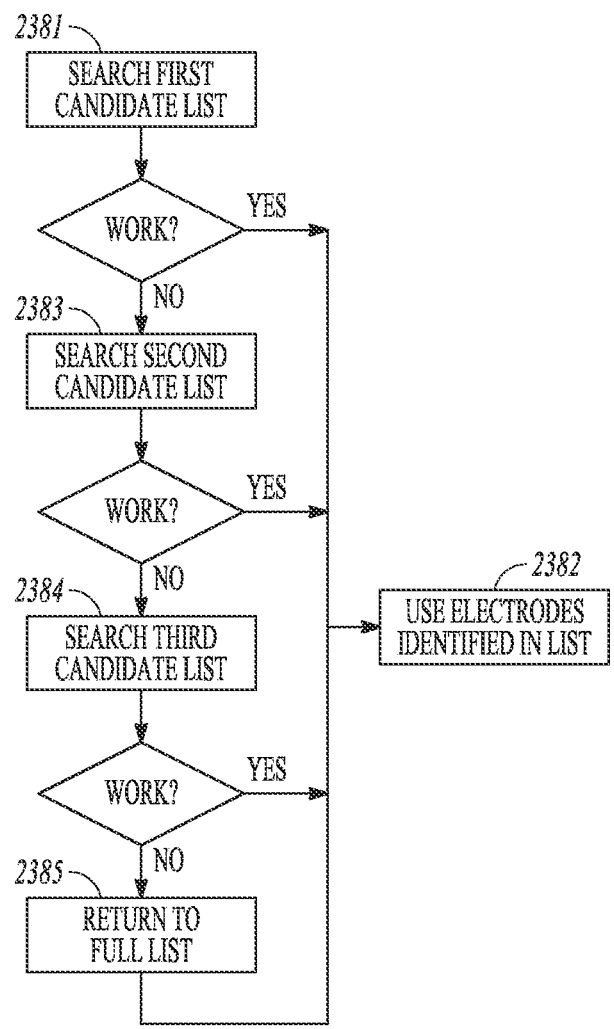
FIG. 23 illustrates, by way of example, aspects of a binary search feature as a rostra-caudal focus feature.

FIG. 23 illustrates, by way of example, aspects of a binary search feature as a rostra-caudal focus feature. A first subset of electrodes that define a first partial lead search region can be tested to determine if the modulation is effective using the first subset 2381. If it is effective, the first subset of electrodes that define the first partial lead search region may be used to deliver the modulation 2382. If it is not effective, then a second subset of electrodes that define a second partial lead search region may be tested to determine if the second subset of electrodes is effective 2383. If it is effective, the second subset of electrodes that define the second partial lead search region may be used to deliver the modulation 2382. If it is not effective, then a third (or nth) subset of electrodes that define a third (or nth) partial lead search region may be tested to determine if the third (or nth) subset of electrodes is effective 2384. If it is effective, the third (or nth) subset of electrodes that define the third (or nth) partial lead search region may be used to deliver the modulation 2382. If it is not effective, then the binary search process may return to the full list of electrodes at 2385 which was previously determined to be effective. At least some of the subsets of electrodes may be exclusive of each other. At least some of the subsets of electrodes may intersect with each other. In some embodiments, at least two subsets are exclusive, and at least one subset has an intersection with another subset.

Figure 24:
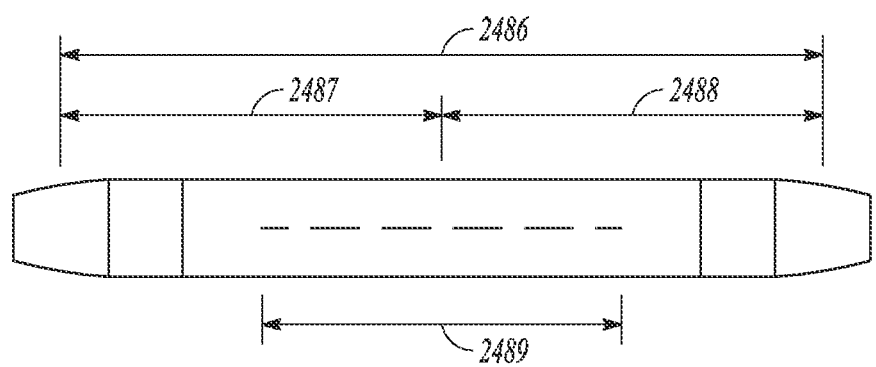
FIG. 24 illustrates an example of the binary search feature.

FIG. 24 illustrates an example of the binary search feature. The lead has a full span 2486 which may be split into three partial lead search regions 2487, 2488 and 2489, each partial search region including a corresponding subset of electrodes. By way of example and not limitation, the first and second subsets 2487 and 2488 of electrodes may be mutually exclusive, and third subset 2489 may include an intersection with the first subset and also may include an intersection with the second set. In an example, the full lead may be bifurcated to provide the first partial lead search region 2487 on a first side of the lead (e.g. left end of electrode array to middle) and the second partial lead search region 2488 on a second side of the lead (e.g. right end of the electrode array to middle). The third partial lead search region 2489 may partially overlap each of the first and second partial lead search regions. Thus, the partial lead search regions may define a first end region, a second end region and a middle region of the lead.

Figure 25A:
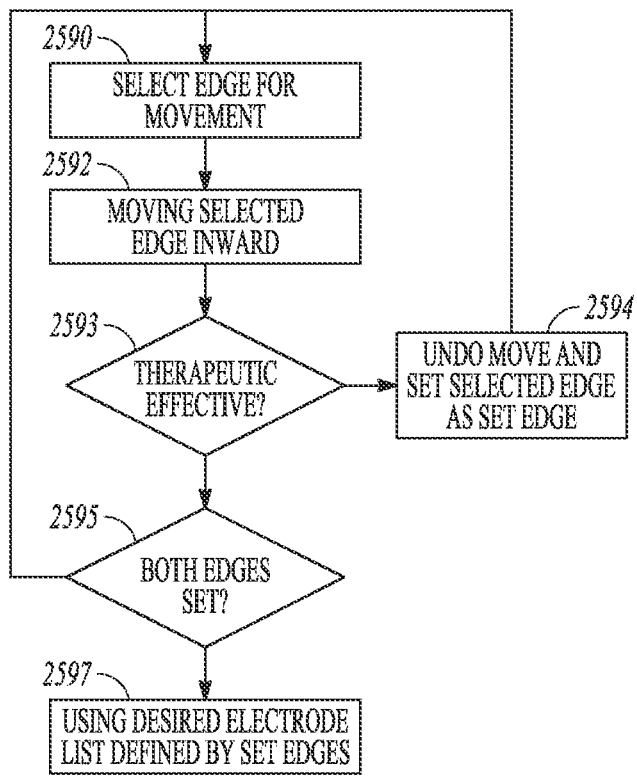
FIG. 25A-25C illustrates, by way of example, an edge search feature as a rostra-caudal focus feature.
Figure 25B:
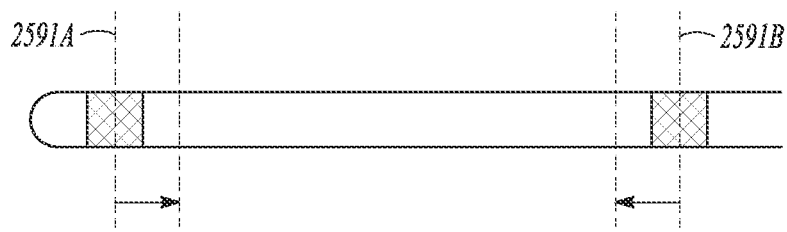
Figure 25C:
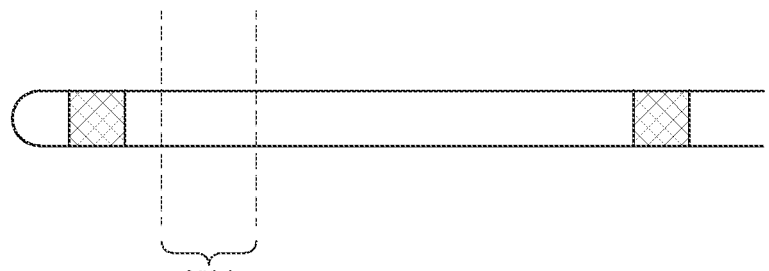

FIG. 25A-25C illustrates, by way of example, an edge search feature as a rostra-caudal focus feature. The edge search feature progressively moves each edge of the active electrodes in the array toward the middle and confirms that the modulation remains effective with the moves. Thus, a first edge can be moved toward the center until the next move toward the center causes the modulation to be ineffective; and a second edge can be moved toward the center until the next move toward the center causes the modulation to be ineffective.

For example, the edge search feature may include selecting an edge of the electrode arrangement (e.g. array) for movement 2590. The selected edge may be one of the two edges 2591A or 2591B illustrated in FIG. 25B. However, there can be more than two edges if more than two regions are being focused. The selected edge is moved inward 2592 toward the other edge for the region of interest. If the reduced set of electrodes is no longer therapeutically effective 2593, then the previous move can be undone and that edge can be set so that is no longer is capable of being selected for movement 2594. The process can return to 2590 to attempt to move the other edge(s). If the reduced set of electrodes continues to be therapeutically effective 2593, then the process returns to 2590 to continue moving edges until such time as all of the edges are set 2595. The final reduced set 2596 of electrodes can be used 2597 to deliver the modulation energy.

According to various embodiments, the programmed system may be configured with a neuromodulation focus feature such as a rostra-caudal focus feature to allow a user to select the desired electrodes for the neuromodulation to be more specific to the desired physiological area. Some embodiments may allow non-contiguous spans to be selected as a result of initial programming and/or neuromodulation refinement later on.

Figure 26:
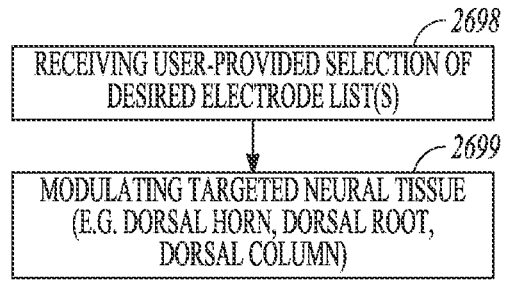
FIG. 26 illustrates, by way of example, a method for selecting an electrode span according to various embodiments.

FIG. 26 illustrates, by way of example, a method for selecting an electrode span according to various embodiments. A user-provided selection of a desired electrode list or lists is received at 2698. The list may include all of the electrodes or may only include some of the electrodes. This may be received using an external device such as a RC or CP. The external device may have a graphical user interface to provide an illustration of the electrodes available for selection. The targeted neural tissue may then be modulated using the electrodes within the desired electrode list(s) 2699. For example, the modulation may be a sub-perception modulation therapy. The targeted neural tissue may be one or more of DC tissue, DR tissue or DH tissue. The sub-perception modulation therapy may be delivered at frequencies at or above 1500 Hz to avoid paresthesia. The sub-perception modulation therapy may be delivered at lower frequencies (e.g. under 1200 Hz, under 1000 Hz, or under 500 Hz) and delivered to preferentially stimulate the DR tissue and/or DH tissue over the DC tissue. By using a reduced electrode list, the power requirements may be decreased without compromising therapeutic effectiveness.

Figure 27:
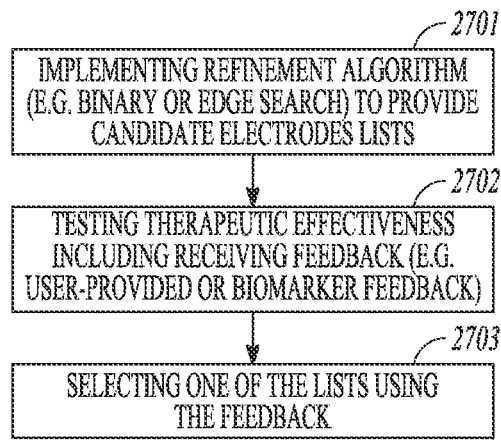
FIG. 27 illustrates, by way of example, a method for further refining the desired electrode lists.

FIG. 27 illustrates, by way of example, a method for further refining the desired electrode lists. A refinement algorithm (e.g. binary search or edge search) may be implemented on the user-provided desired electrode list to provide candidate electrode lists 2701. The therapeutic effectiveness of the candidate electrode lists may be tested, which may include receiving user provided feedback or biomarker feedback 2702. One of the candidate electrode lists may be selected based on therapeutic effectiveness as determined using the feedback 2703.

Figure 28:
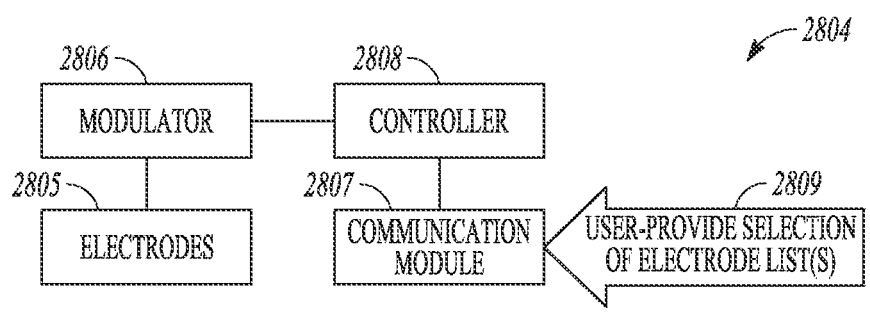
FIG. 28 illustrates, by way of example, a system such as may be implemented to receive user-provided selection of electrodes list(s).

FIG. 28 illustrates, by way of example, a system such as may be implemented to receive user-provided selection of electrodes list(s). The illustrated system 2804 includes an arrangement of electrodes 2805 configured to be operationally positioned for use in modulating targeted neural tissue, a neural modulation generator 2806 configured to use at least some electrodes within the arrangement of electrodes to generate a modulation field, a communication module 2807 configured to receive user-provided selections, and a controller 2808. The controller 2808 may be configured to use the communication module 2807 to receive a user-provided selection of a desired electrode list 2809. The electrode list identifies electrodes within the arrangement of electrodes that are available for use in modulating the targeted neural tissue. The controller 2808 may control the neural modulation generator to generate the modulation field, and use the electrodes identified in the electrode list to modulate the targeted neural tissue. The modulation may be a sub-perception modulation. The neural modulation generator may use modulation parameter set to promote uniformity of a modulation field within targeted tissue using the reduced subset of electrodes identified in the electrode list. The controller may be configured to implement a refinement algorithm (e.g. binary search and/or edge search) to further reduce the electrode list(s). The system may include a feedback module to receive feedback regarding the therapeutic effectiveness for at least one candidate electrode list. The feedback module may be configured to receive user-provided feedback regarding the therapeutic effectiveness to relieve pain. In addition or alternatively, the feedback module may be configured to detect a biomarker signal regarding the therapeutic effectiveness.

Calibration of Sub-Perception Modulation

Sub-perception modulation can also pose some challenges for calibrating the modulation therapy as the patient does not perceive the delivery of the modulation energy. Calibration may include sensor(s), such as discussed in U.S. Provisional Application No. 62/054,076 filed on Sep. 23, 2015 and incorporated by reference in its entirety. Examples of sensors include quantitative sensory testing (QST), electroencephalogram (EEG), electrocorticogram (ECoG), diffuse optical imaging, functional magnetic resonance imaging (fMRI), local filed potentials (LFPs) in axons, and evoked compound action potentials (eCAPs) in axons.

Calibration of sub-perception modulation may use patient perception and an automated or semi-automated field troll that moves a modulation field through positions within in a volume of a targeted tissue. A sub-perception programming algorithm may use information about the relative excitation threshold as a function of electrode position. If sensing is available, a compound action potential (e.g. a compound action potential sensed in the dorsal column) may be used. In the absence of sensing, calibration requires user feedback. However, manual calibration in a standard SCS programming session is too slow.

Various embodiments automatically troll a modulation field along the lead. A patient may be instructed to keep the intensity of the perceived modulation to remain constant using a patient input to adjust the modulation intensity (e.g. amplitude, pulse width, etc.) of the modulation. The patient may be instructed to keep the intensity of the perceived modulation at a perception threshold, or at a higher level of perception (e.g. just below the patient's ability to tolerate the perceived modulation), or at another level of perception. The patient input may be a variety of input types, such as but not limited to objects displayed on a touch screen, buttons, dials and slides.

The trolling of the modulation field may be automatic or through patient control. Candidate trolling algorithms include a monopolar troll (anodic or cathodic) or a bipolar troll or a multipolar troll. The troll can be done with MICC or multiple independent voltage control, or with a timing channel interleaving technique. MICC enables the locus of the modulation to be gradually moved across along the lead or within the array of electrodes. The interleaving of timing channels allows different electrode(s) in different timing channels. Values of stimulation parameter(s) (e.g. amplitude) in the timing channels can be adjusted. Thus by way of example and not limitation, if a monopolar modulation is delivered using a first electrode in a first channel and another monopolar modulation is delivered using a second electrode adjacent to the first electrode in a second channel, then the amplitude of the monopolar modulation in the first channel may be incrementally reduced as the amplitude of the monopolar modulation may be increase in the second channel. In this matter, the locus of the modulation may be gradually reduced.

Some embodiments may provide a threshold calibration automation mode. A modulation field may be generated, and the patient may be instructed to attain perception threshold and may be given control to select an automatic increase or decrease of amplitude and to mark when amplitude reaches a perception threshold. In some embodiments, the patient may be given a control to adjust the current amplitude and pulse width during the trolling routine while the system keeps the user inside of a strength-duration curve defined for the system. The marking of a perception threshold may cause the device to automatically switch to the next electric field.

The intensity data (e.g. amplitude values) that causes a constant level or range of patient-perception along the lead or within an array of modulation electrodes can be used directly or in a model (to smooth, eliminate outlying points, etc.) to estimate relative excitation as a function of the position along the lead.

This calibration data may be input into the modulation algorithm and a field is defined. A manual mode may also be used, where after each marking, some embodiments may keep the next configuration at the same amplitude as the previous configuration, allowing the user to adjust to perception threshold. Some embodiments may reduce the current when the trolling proceeds to the next position (e.g. electrode) of interest. The current reduction may be a fraction of the previous current. The fraction may be selected to reduce the current to a level that is likely just below the threshold perception such that an up-titration routine can be implemented to quickly find the perception threshold. By way of example and not limitation, the fraction may be between 50% and 99% of the previous current. The switch between configurations may be automated or semi-automated with the user selecting to switch configuration.

Figure 29:
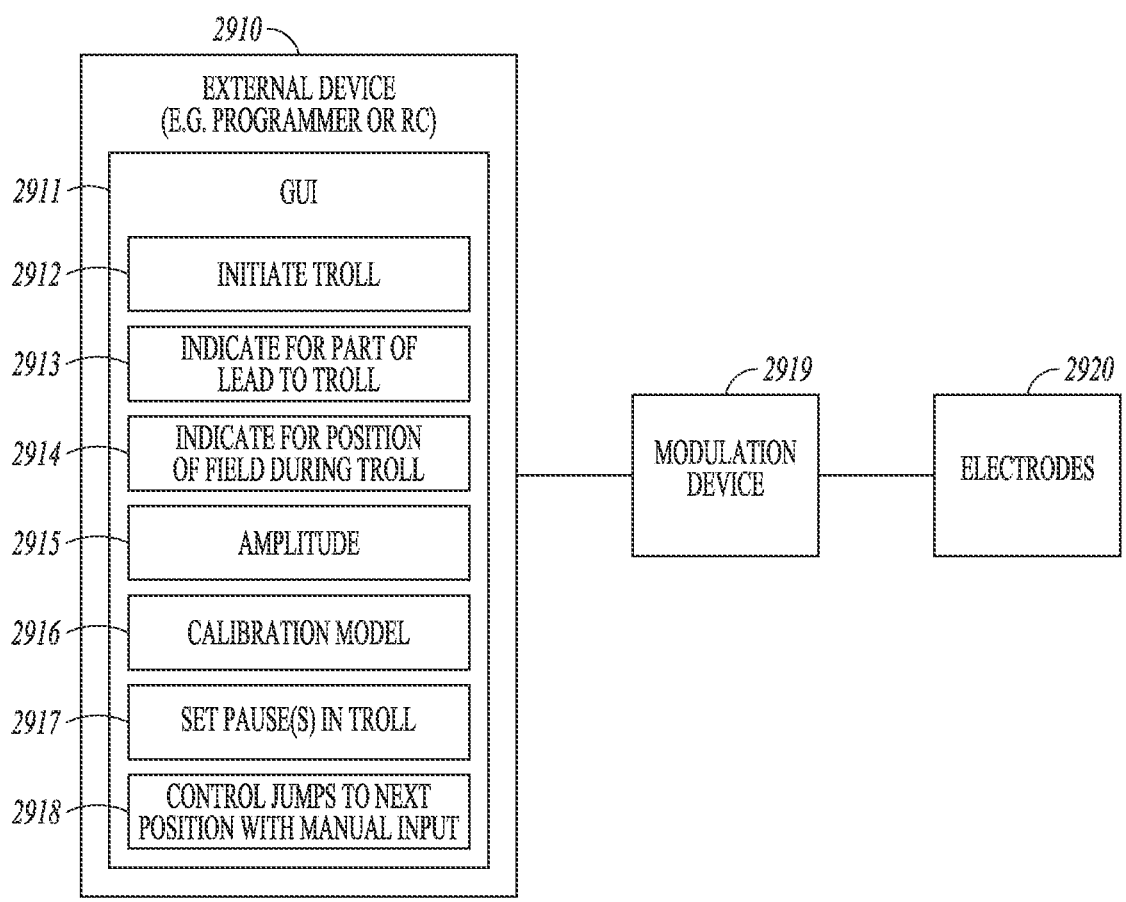
FIG. 29 illustrates, by way of example, an example of a system that may be used to implement field troll.

FIG. 29 illustrates, by way of example, an example of a system that may be used to implement field troll. A external device 2910, such as a CP or a RC, may be used by a user (e.g. clinician or patient) to input the patient's perception of the modulation field. The external device may include a graphical user interface (GUI) 2911 with GUI elements to implement the calibration. These GUI elements may include: a button or control to initiate the automated troll 2912; graphical indicators on a graphical lead reference to indicate what part of the lead to troll 2913; a graphical indicator to show the position of the field on the lead during the automated troll 2914; a graphical indicator of the user chosen amplitude from the automated troll (generated real-time, or subsequent screen) 2915; a graphical indicator of the calibration model (if a model is used) 2916; controls to set or modify the speed of the automated troll (can be quantitative—e.g., number of seconds, or qualitative—e.g., slow, medium, fast) 2917; ability to set one or more pauses in the automated troll (e.g., hold the field for a few seconds at the contacts to get more data at those points or control the jump to the next auto troll location with manual input) 2918. The illustrated system further includes a modulation device 2919 and an electrode arrangement 2920 for use to generate and move the modulation field within the volume of targeted tissue. The amplitude of the current may be increased or decreased according to the user-input.

Figure 30:
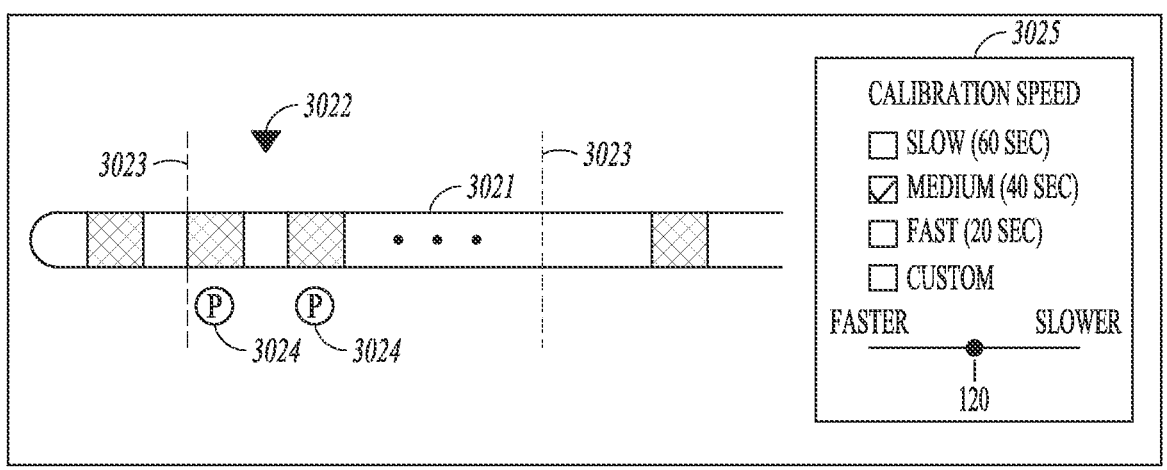
FIG. 30 illustrates, by way of example, an example of a GUI of an external device used in the performance of the field troll.

FIG. 30 illustrates, by way of example, an example of a GUI of an external device used in the performance of the field troll. The GUI may provide an illustration of the lead 3021 or the electrode arrangement or the targeted tissue. The GUI may provide a real-time or near real-time indicator of the position of the modulation field 3022. The position may be a relative position to the illustrated lead or illustrated electrode arrangement or illustrated target tissue. A user may use the GUI to set boundaries of the troll 3023 and/or pause points 3024 for areas of interest to allow additional data to be collected. For example, these points may be controlled via drag and drop. The GUI may allow the user to select the speed of the calibration 3025. By way of example and not limitation, the user may select predefined speed (e.g. slow, completing calibration in 60 seconds; medium, completing calibration in 40 seconds, or fast, completing calibration in 20 seconds.) The GUI may allow the user to provide a custom speed. For example, the GUI may allow the user to select any speed between a fast limit and a slow limit for the calibration.

Various embodiments troll a modulation field, using an arrangement of electrodes on at least one lead, through neural tissue positions, and perform a marking procedure multiple times as the modulation field is trolled through the positions. The marking procedure identifies when the modulation field provides patient-perceived modulation. The marking procedure may include receiving a marking signal that indicates that a modulation intensity achieved the patient-perceived stimulation, and storing modulation field parameter data that affects the modulation intensity in response to receiving the marking signal. The modulation intensity may include modulation parameters that affect the patient's perception of the modulation energy. These parameters may include pulse width, rate, amplitude, distribution of current, and electrode polarity (cathode v. anode). Paresthesia is one example of a way in which the patient may perceive the modulation energy. By way of example and not limitation, the storage of the modulation field parameter data may be in a temporary storage such as but not limited to cache or RAM or in permanent/persistent storage such as but not limited to ROM, a memory device such a hard drive, optical disc, thumb drive, or cloud storage.

Modulation parameter values may be used to estimate relative excitation of neural tissue as a function of neural tissue position. The estimated relative excitation may be used to program modulation energy to be delivered through one or more electrodes in the arrangement of electrodes.

The marking process may include receiving a titration signal that indicates an instruction to adjust modulation intensity, adjusting the modulation intensity in response to receiving the titration signal, and receiving the marking signal that indicates the adjusted modulation intensity achieved the patient-perceived modulation. The titration signal may be initiated by a patient, or by a clinician or other user who is responding to patient responses. After receiving the marking signal, a subsequent marking process may begin at the adjusted modulation intensity. The subsequent marking process may include subsequently adjusting the adjusted modulation intensity in response to receiving a subsequent titration signal, and receiving a subsequent marking signal that indicates the subsequently-adjusted modulation intensity achieved the patient-perceived modulation.

Some system embodiments may include an implantable device and an external device. The implantable device may include the neural modulation generator, the communication module, the memory and the controller. The external device may be configured to send commands to the implantable device and provide a graphical user interface. The graphical user interface may be configured to provide a current amplitude control configured to adjust the current amplitude during the trolling routine or to provide a current and pulse width control configured to adjust the current amplitude and pulse width during the trolling routine. The system may be configured to keep the user inside of a strength-duration curve defined for the system. The graphical user interface may also provide any one or any combination of the following controls: a trolling start configured to initiate the trolling routine; a speed control configured to set or modify a speed for changing positions during the trolling routine; a resolution control to specify a step size for trolling; or a pause control configured to set one or more pauses in the trolling routine. The graphical user interface may also or alternatively provide at least one of a graphical lead indicator configured to indicate a part of the array of electrodes to troll during the trolling routine, or a graphical field indicator to indicate the position of the field during the trolling routine. The graphical field indicator may also indicate the extent of the field in the different positions during the trolling routine.

The titration signal may include a manually-initiated titration signal that is manually-initiated by the user. Alternatively or additionally, the titration signal may include an automatically-provided signal to automatically adjust the modulation intensity. The automatically-provided signal may be controlled by programmed instructions to automatically adjust the modulation intensity according to scheduled times or after expiration of a timer or after receipt a marking signal. The system may be configured to receive a user-provided command to stop the automatic adjustment of the modulation intensity.

Trolling the modulation field may include automatically moving the modulation field. For example, a marking signal may be generated when a count-down timer expires while the modulation intensity is being adjusted. In some embodiments, the count-down timer may be extended by the user and/or accelerated by the user to proceed immediately to the next trolled position. The count-down timer may have different durations to provide for longer duration at points of interest in the trolled positions and shorter duration at other troll positions. The count-down timer maybe displayed to the user using a timer clock or using other indicators such as progress bars, color gradient, intensity levels of display, etc. Trolling the modulation field may include a patient-controlled movement of the modulation field, or some combination of automatic and patient control in a semi-automatic troll.

Trolling the modulation field may include moving a monopolar modulation field in which a case electrode is configured as an anode and electrodes within the arrangement of electrodes are configured as cathodes, or the case electrode is configured as a cathode and the electrodes within the arrangement of electrodes are configured as anodes, or the electrodes within the arrangement of electrodes are configured as anodes or cathodes. However, the present subject matter is not limited to monopolar modulation, as bipolar or multipolar modulation maybe used to troll the field through the positions of the targeted tissue. Trolling the modulation field may include changing fractionalized current values for electrodes within arrangement of electrodes to move the modulation field through neural tissue positions. Trolling the modulation field may include using at least one timing channel to generate at least two different fields to the patient. The stored modulation parameter data may be directly used to estimate relative excitation of neural tissue as a function of neural tissue position. In some embodiments, a model is implemented to estimate the relative excitation using the stored modulation field data as inputs to the model.

Patient-perception to modulation, such as paresthesia, can be used to calibrate a sub-perception therapy. For example, a pulse amplitude may be increase to achieve paresthesia or another patient-perceived indicator of the delivered modulation energy. Examples of other patient-perceived indicators may include temperature, proprioception, general discomfort, pressure, itch, pulling, vibration and the like. The system may be configured to calibrate sub-perception therapy using a threshold for the patient to perceive the modulation or a threshold for the patient to tolerate the modulation or another perceived range of modulation intensity. The modulation device may be programmed with an amplitude that is a fraction of the patient-perception current. However, for small pulse width programs, the amplitude required to achieve paresthesia is often higher than that achievable with modulation output constraints for implantable stimulators. Sub-perception modulation may modulate DC, DR and/or DH tissue. Sub-perception modulation may include frequencies of about 1500 Hz or greater. Sub-perception modulation may preferentially modulate DH and/or DR tissue over DC tissue at frequencies lower than 1500 Hz (e.g. lower than 1200 Hz such as but not limited to frequencies within a range between 2 Hz and 1200 Hz, or lower than 1000 Hz, or lower than 500 Hz).

Curve fitting techniques, such as Lapique strength duration model or Weiss charge duration model, may be used to estimate strength-duration curves from sparse data. The data may be plotted as charge vs. duration and a linear curve fit is employed. The parameters of the linear fit are used to estimate chronaxie and rheobase current and to construct the model strength duration curve.

Figure 31:
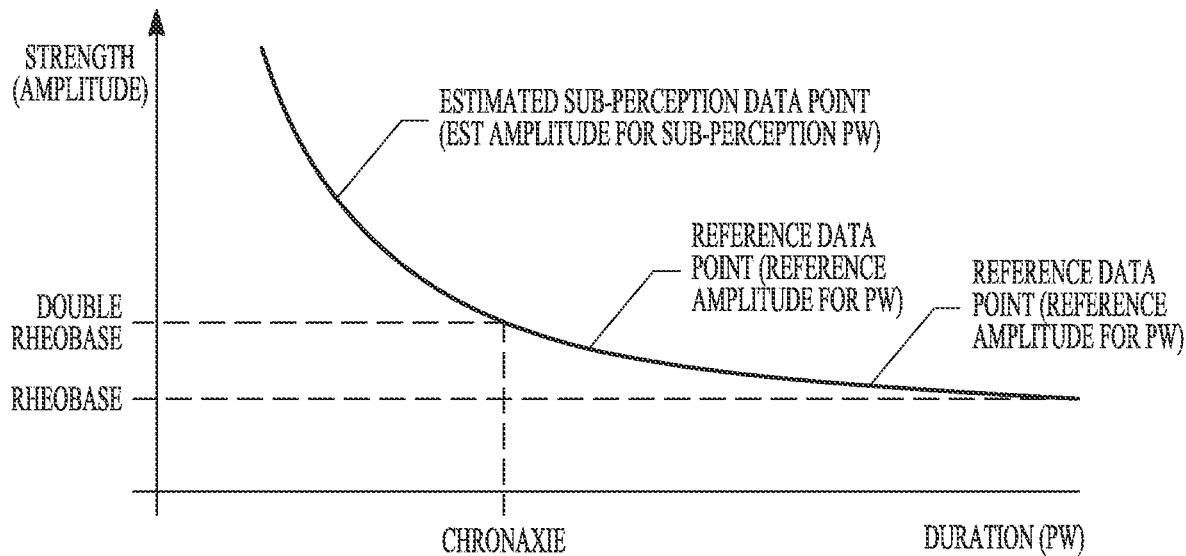
FIG. 31 illustrates, by way of example, an example of the strength duration curve, in which an amplitude of a pulse (strength) is plotted against a duration (pulse width) of the pulse.

FIG. 31 illustrates, by way of example, an example of the strength duration curve, in which an amplitude of a pulse (strength) is plotted against a duration (pulse width) of the pulse. The stimulation of a membrane depends on both the strength and duration of the stimulus. The plot indicates that, as pulse width decreases, the required current amplitude increases. The plot also illustrates rheobase and chronaxie. Rheobase represents a minimal current of infinite duration that causes an action potential, and chronaxie is the minimum time for a current double the rheobase to cause an action potential. Two or more reference data points measured for larger pulse widths can be used to identify the strength duration curve, and this curve can be used to estimate the current that corresponds to smaller pulse widths. Thus, various embodiments obtain thresholds for larger pulse widths at which the stimulator is capable of generating an intensity that allows the patient to perceive a modulation threshold, and then use these thresholds for large pulse widths to estimate, using a strength duration curve, the perception threshold for smaller pulse widths for which the stimulator is not capable of generating an intensity that the patient will perceive. As an alternative or in addition to using the threshold of patient perception, other perception values may be used. For example, a tolerance threshold may be used where the tolerance threshold indicate a largest amount of modulation energy that can tolerate. A proportion of this estimated threshold may be used for the neural modulation program setting. Thus, data can be acquired to fit the desired small pulse widths.

Figure 32:
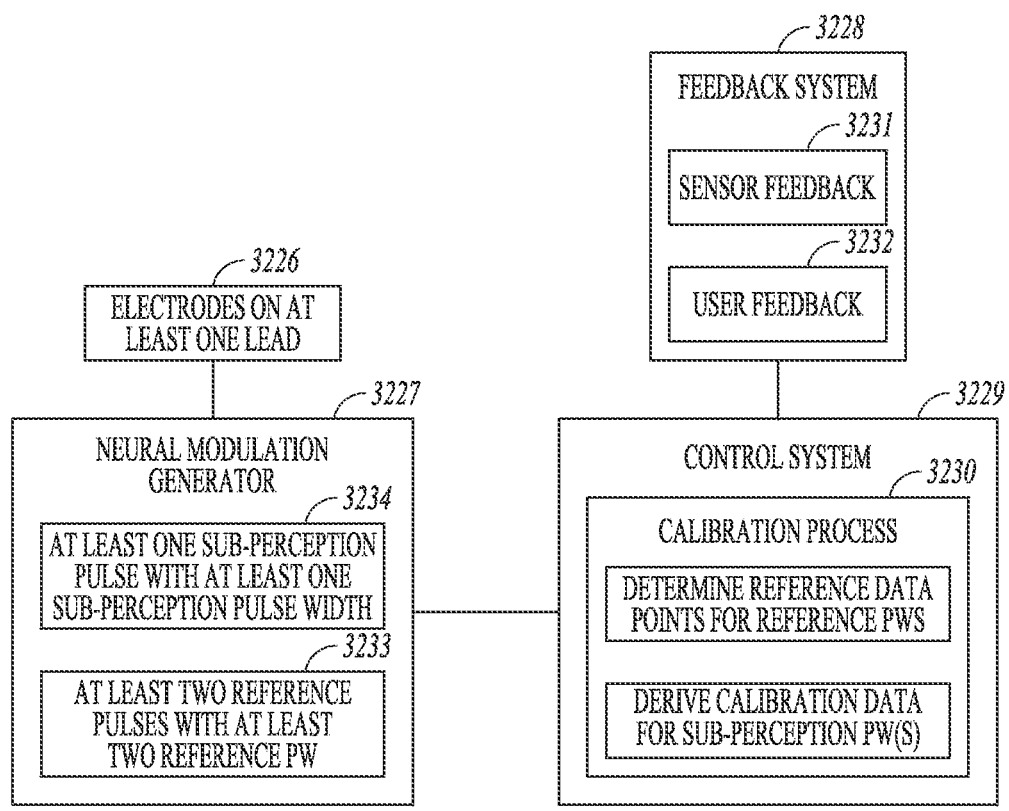
FIG. 32 illustrates, by way of example, an embodiment of a system that may be used to calibrate sub-perception modulation at low pulse widths.

FIG. 32 illustrates, by way of example, an embodiment of a system that may be used to calibrate sub-perception modulation at low pulse widths. The illustrated system may include electrodes 3226 on at least one lead configured to be operationally positioned for use in delivering sub-perception neural modulation. The system may further include a neural modulation generator 3227 configured to use at least some electrodes to generate a modulation field for the sub-perception neural modulation. The system may include a feedback module 3228 configured to receive a signal that a generated modulation field provides patient-perceived modulation, and a control system 3229 operably connected to the neural modulation generator 3227 and the feedback system 3228 and configured to implement a calibration process 3230. The feedback system 3229 may include sensor feedback 3231 and/or user feedback 3232 via external device(s) such as user feedback that the patient has experienced paresthesia. Examples of a feedback sensor may include a sensor to sense an evoked compound action potential or other measurable biomarker. The calibration process implemented by the control system 3229 may include controlling the neural modulation generator 3227 to generate the modulation field using two reference pulses 3233 including a first stimulus pulse with a first pulse width and a second stimulus pulse with a second pulse width. The control system 3229 may use the feedback module 3228 to determine a first reference point that represents an intensity of the modulation field generated using the first pulse width that provides the patient-perceived modulation, and use the feedback module to determine a second reference point that represents an intensity of the modulation field generated using the second pulse width that provides the patient-perceived modulation. Sub-perception calibration data may be derived using at least the first and second reference data points. Deriving sub-perception calibration data includes deriving sub-perception calibration data specific to sub-perception delivered using a sub-perception pulse with a sub-perception pulse width 3234.

Figure 33:
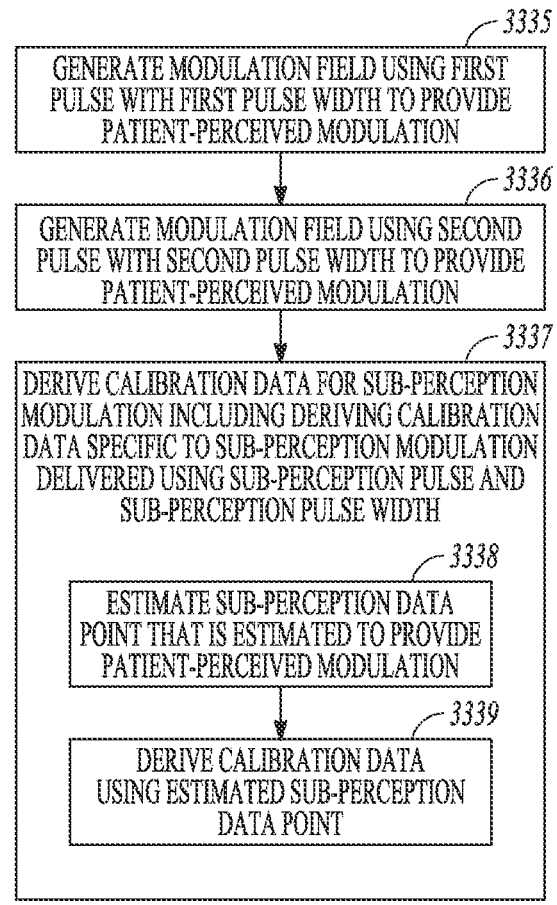
FIG. 33 illustrates, by way of example, an embodiment of a process for programming sub-perception modulation with a short pulse width.

FIG. 33 illustrates, by way of example, an embodiment of a process for programming sub-perception modulation with a short pulse width. As illustrated at 3335, a modulation field may be generated using a first stimulus pulse with a first pulse width. A first reference data point may be determined, where the first reference data point represents an intensity of the modulation field generated using the first pulse width that provides patient-perceived modulation. As illustrated at 3336, the modulation field may be generated using a second stimulus pulse with a second pulse width. A second reference data point maybe determined, where the second reference data point represents an intensity of the modulation field generated using the second pulse width that provides the patient-perceived modulation. As illustrated at 3337, calibration data for sub-perception modulation may be derived using at least two reference data points including the first and second reference data points. Deriving calibration data may include, as illustrated at 3338, estimating a sub-perception data point that represents an estimated intensity of the modulation field generated using the sub-perception pulse width that is estimated to provide the patient-perceived modulation. The estimated sub-perception data point may be extrapolated from the at least two reference data points. Deriving calibration data may further include, as illustrated at 3339, deriving the calibration data (e.g. amplitude) for sub-perception using the estimated sub-perception data point. For example, the amplitude for a small pulse width, sub-perception pulse may be a fraction of the amplitude the estimated sub-perception data point.

Estimating the sub-perception amplitude for the sub-perception pulse width may include applying a curve fitting technique on the first and second reference amplitudes to identify curve parameters for a charge duration model curve, and using the first and second reference amplitudes and the charge duration model curve to estimate the sub-perception for the sub-perception pulse width that provides the patient-perception threshold. Examples of curve parameters include chronaxie and rheobase current. The curve fitting technique may include a Lapique strength duration model or Weiss charge duration model or other exponential or inverse proportionality model, and the reference data points may represent a pulse width and a current amplitude of the pulse width.

This approach may be used with DH or DR stimulation or with any time of stimulation where needs to estimate the amplitude of stimulation from something known, but is unable to reach the something known at smaller pulse widths. For example, a method may comprise generating a modulation field using a first stimulus pulse with a first pulse width and determining a first reference data point that represents a modulation intensity generated using the first pulse width that provides a perceived or measurable response, and generating the modulation field using a second stimulus pulse with a second pulse width and determining a second reference data point that represents a modulation intensity of the modulation field generated using the second pulse width that provides the response. Calibration data for the modulation may be derived using at least two reference data points including the first and second reference data points. Deriving calibration data may include deriving calibration data specific to modulation delivered using a pulse with a pulse width smaller than the first and second pulse widths. Deriving the calibration data may include estimating a data point that represents an estimated intensity of the modulation field generated using the smaller pulse width that is estimated to provide the response. The estimated data point may be extrapolated from the at least two reference data points. The calibration data may be derived using the estimated sub-perception data point.

In contrast to a supra-perception therapy, a sub-perception therapy has specific needs in terms of how the patient interacts with the implant using an external device such as an RC. For example, the dose control (amplitude, burst on/off, frequency, etc.) of the sub-perception therapy is not related to a direct paresthesia perception but the dose control still may have a negative effect in the therapy if not properly managed. Various embodiments provide features in the external device (e.g. RC) to allow the patient to adjust the therapy to improve outcomes without requiring intervention by a clinician. The patient may initiate a self-calibration as well as control dose features like burst modulation.

The perception threshold and/or preferred modulation paradigm may be different for different patient postures. Various embodiments provide sub-perception therapy that is adaptive to accommodate posture variations during the daily life of the patient.

Various embodiments provide an automatic recalibration feature. The automatic recalibration feature may be configured to automatically re-run the calibration routine when patient posture change is detected through sensed signal such as an accelerometer, evoked compound action potentials (ECAP), field potentials including local field potentials (LFP), impedance, and others). The calibration information from the calibration routine may be used to adjust the modulation program.

Various embodiments provide a semi-automated calibration feature. A patient can initiate recalibration when the patient changes posture. The calibration information from the calibration routine may be used to adjust the modulation program.

Various embodiments provide an adaptive modulation feature. The adaptive modulation feature may include a posture-adaptive feature configured to set up different sets of programmable parameters, where each set is specific for posture position. The system may be configured to switch to the corresponding program when patient posture change is detected.

Various embodiments provide an adaptive modulation feature that includes an activity-adaptive feature configured to set up different sets of programmable parameters, where each set is specific for an activity level. The activity level may be sensed using external or internal activity sensors.

The adaptive modulation feature may include a posture-adaptive and activity-adaptive feature configured to set up different sets of programmable parameters for different combinations of posture and activity. The system may be configured to switch to the corresponding program when patient posture change and/or patient activity change is detected. For example, the system may be configured to calibrate modulation to provide desirable modulation parameters specific for situations such as, by way of example and not limitation, bed time, normal activity and high intense activity level.

Figure 34:
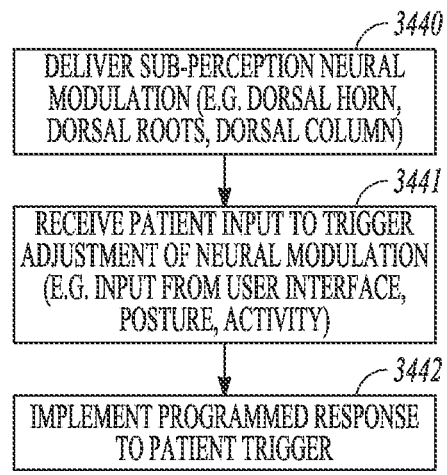
FIG. 34 illustrates, by way of example, an embodiment of a method that includes delivering sub-perception modulation.

FIG. 34 illustrates, by way of example, an embodiment of a method that includes delivering sub-perception modulation. At 3440, the sub-perception neural modulation is delivered to neural tissue using an implantable device and electrodes. The neural tissue may include at least one of dorsal horn tissue, dorsal root tissue or dorsal column tissue. The sub-perception modulation has an intensity below a patient-perception threshold, where the patient-perception threshold is a boundary below which a patient does not sense generation a modulation field. For example, the patient-perception threshold may be a threshold at which a patient experiences paresthesia. At 3441 patient input is received to trigger an adjustment to the neural modulation. The patient may provide input through a user interface of an external device. The patient input may be a sensor input that senses a parameter of state of the patient. At 3442 a programmed response to the patient trigger is implemented to adjust the neural modulation.

By way of example, the patient input may be a user-requested dose adjustment and the response may be a response that adjusts the dose of the neural modulation. In some embodiments, the programmed response includes modulation limits that limit the ability to adjust the modulation. An example of such a limit is a safety limit to avoid potentially unsafe dosages of neural modulation. In some embodiments, the programmed response includes receiving feedback to assess therapeutic effectiveness of the neural modulation, and automatically self-calibrating the neural modulation using the received feedback input. The feedback may be a patient-provided indication of pain relief that is provided using the user interface of the external device. The feedback may include a signal from a sensor to assess therapeutic effectiveness of the neural modulation.

The received patient input may be a received patient activity. The patient activity may be sensed using an activity sensor such as an accelerometer-based activity sensor. The patient activity level may be received by a user-input. For example, the patient may enter activity information into an external device (e.g. RC) to monitor the patient's activity. The method may include automatically assessing a quality of patient health using the patient activity level input, and triggering the adjustment to the neural modulation when indicated by the assessed quality of health. Triggering the adjustment when indicated by the assessed quality of health may include triggering a calibration routine to calibrate or recalibrate the neural modulation.

Figure 35:
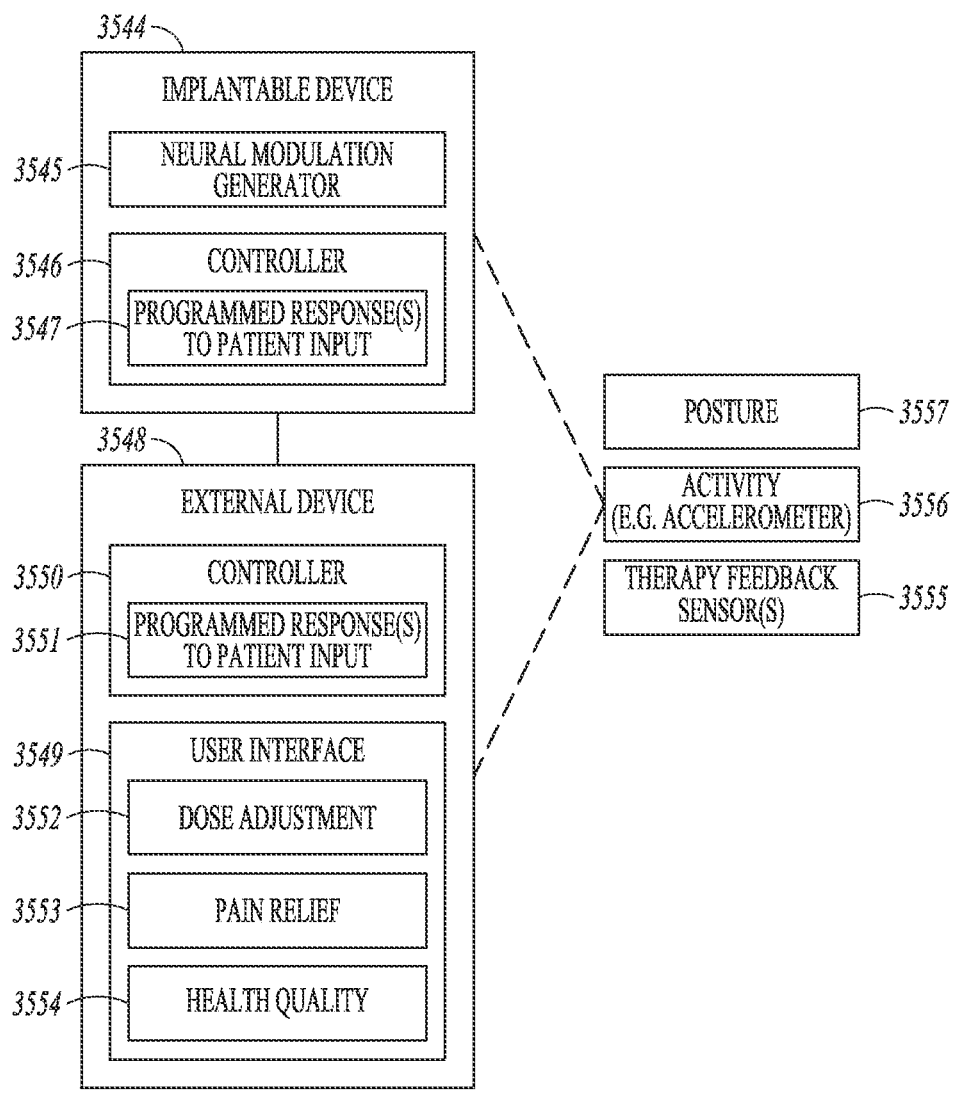
FIG. 35 illustrates, by way of example, a system that delivers sub-perception modulation.

FIG. 35 illustrates, by way of example, a system that delivers sub-perception modulation. The system may include an arrangement of electrodes configured to be operationally positioned for use in modulating neural tissue. The neural tissue may include at least one of dorsal horn tissue, dorsal root tissue or dorsal column tissue. The system may further include, as illustrated, an implantable device 3544 including a neural modulation generator 3545 configured to use at least some of the electrodes 3543 to generate a modulation field to deliver sub-perception modulation to the neural tissue. The system may include a controller 3546 configured to control the neural modulation generator 3545 to generate the modulation field, and implement programmed responses 3547 to automatically adjust the modulation field in response to a patient input. The system may include an external device 3548 configured to communicate with the implantable device 3544. The external device 3548 may include a user interface 3549 to receive the patient input, and a controller 3550 configured to implement a programmed response or responses 3551 to patient input, automatically initiating communication to send a patient-initiated control signal from the external device 3548 to the implantable device 3544. The controller 3546 of the implantable device 3544 may be configured to control the neural modulation generator 3545 to generate the modulation field, and automatically adjust the modulation field in response to the patient-initiated control signal.

The patient may use the user interface 3549 to provide a dose adjustment 3552. The controller 3546 of the implantable device 3544 may be configured to automatically adjust a dose of the neural modulation in response to the patient-initiated control signal. The system may be configured to limit the automatic adjustment of the dose in response to the patient-initiated control signal. The external device 3548 and/or implanted device 3544 may be configured with feature(s) to limit dose adjustment.

The system may further include a feedback input to assess therapeutic effectiveness of the neural modulation. For example, the feedback may relate to user-provided pain relief or user-provided health quality. The system may be configured to automatically self-calibrate the neural modulation using feedback received at the feedback input. The feedback input may include a user-interface of an external device (e.g. a GUI of an RC) used to receive inputs from a user (e.g. patient or clinician or other caregiver) regarding the effectiveness of the therapy. For example, the user may provide an indication of pain relief 3553 or health quality 3554 using the user interface of the external device. The feedback input may include a therapy feedback sensor 3555 to sense a parameter that is indicative of therapeutic effectiveness. There may be multiple feedback sensors.

The patient input may include a patient activity input 3556. The controller may be configured to automatically trigger a calibration routine when indicated by a quality of patient health that may be derived using the patient activity input. By way of illustration, a significant lowering in activity may indicate that the therapy is not effective (e.g. patient is experiencing a significant amount of pain) such that the patient is not performing his or her normal activities. This may indicate that the modulation therapy should be recalibrated to address lead migration or other changes. A significant increase in activity (or maintaining a significant level activity) may indicate that the therapy is effective (e.g. the patient is not experiencing a significant amount of pain).

The patient input may include a patient posture input 3557. In some embodiments, the controller may be configured to automatically trigger a calibration routine when indicated by a quality of patient health that may be derived using the patient posture input. input. By way of illustration, a significant change in posture (or unusual posture during a given time of day) may indicate that the therapy is not effective (e.g. patient is experiencing a significant amount of pain) such that the patient is not performing his or her normal activities. For example, a patient may be sitting or lying down during times when the patient is normally standing or walking. This may indicate that the modulation therapy should be recalibrated to address lead migration or other changes.

In some embodiments, the controller may alternatively or additionally be configured to implement a calibration routine to generate calibration data for a detected patient posture, and adjust a stimulation program using the generated calibration data for the detected patient posture. In some embodiments, the controller may alternatively or additionally be configured to implement a calibration routine to generate calibration data for a detected patient activity, and adjust a stimulation program using the generated calibration data for the detected patient activity.

Figure 36:
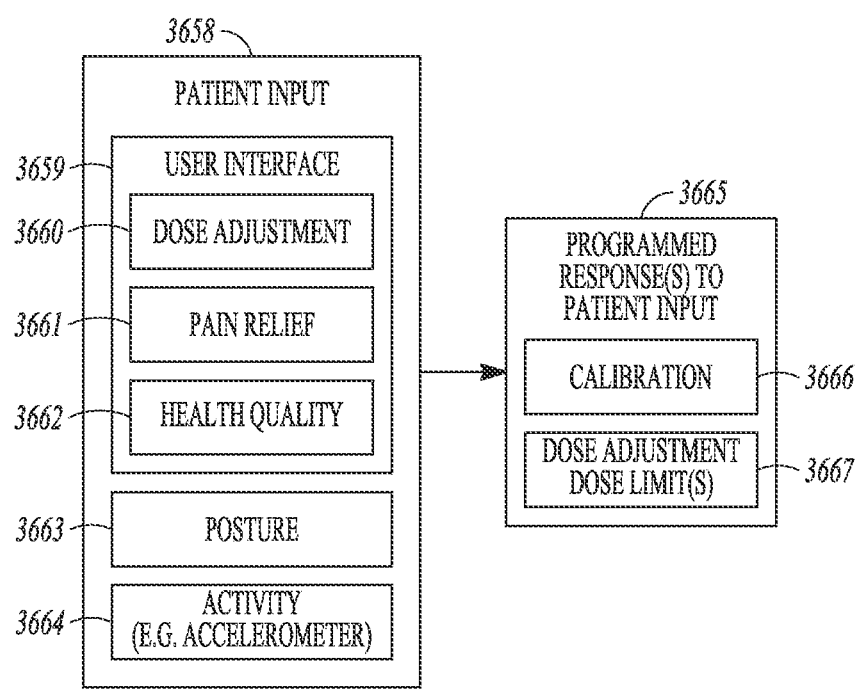
FIG. 36 illustrates an example of programmed response(s) to patient input(s).

FIG. 36 illustrates an example of programmed response(s) to patient input(s). The patient input 3658 may be inputted through a user interface 3659 to provide inputs such as a user-inputted dose adjustment 3660, a user-inputted pain relief 3661, or a user-inputted health quality 3662. Alternatively or additionally, the patient inputs may include sensed posture 3663 and/or sensed activity 3664. The programmed response(s) 3665 may include, by way of example and not limitation, calibration or recalibration 3666, and/or dose adjustment 3667 with or without limits to the dose adjustment. In some embodiments, the calibration may be performed for a specific posture range or specific activity range, and be used to create a modulation parameter set specific for that specific posture range or specific activity range. The above detailed description is intended to be illustrative, and not restrictive. The scope of the disclosure should, therefore, be determined with references to the appended claims, along with the full scope of equivalents to which such claims are entitled.

What is claimed is:

1. A method for modulating a volume of tissue to promote uniformity of a modulation response in the volume of tissue, wherein the volume of tissue has an activation function characterizing the volume of tissue's response to electrical modulation, the method comprising:
   selecting, using a user interface, a modulation field to electrically modulate the volume of tissue that has the activation function, wherein selecting the modulation field includes selecting an objective function for the modulation field that is specific to the volume of tissue and the activation function of the volume of tissue to promote the uniformity of the modulation response in the volume of tissue to the modulation field, wherein the objective function identifies characteristics of the modulation field for modulating the volume of tissue;
   programming a neuromodulator with modulation parameters determined, using both the objective function and the activation function, to promote the uniformity of the modulation response in the volume of tissue; and
   using the neuromodulator programmed with the modulation parameters to modulate the volume of tissue using the selected modulation field with the selected objective function specific to the volume of tissue and the activation function of the volume of tissue to promote the uniformity of the modulation response in the volume of tissue.

2. The method of claim 1, wherein selecting the objective function for the modulation field includes selecting an objective function to modulate dorsal horn tissue.

3. The method of claim 2, wherein selecting the objective function for the modulation field further includes selecting a constant E objective function to modulate the dorsal horn tissue.

4. The method of claim 2, wherein selecting the objective function for the modulation field further includes selecting a constant |E| objective function to modulate the dorsal horn tissue.

5. The method of claim 1, wherein selecting the objective function for the modulation field includes selecting an objective function to modulate dorsal column tissue.

6. The method of claim 5, wherein selecting the objective function to stimulate dorsal column tissue includes selecting a constant activation function to modulate dorsal column tissue.

7. The method of claim 6, wherein selecting the constant activation function to modulate dorsal column tissue includes selecting a constant voltage to modulate dorsal column tissue.

8. The method of claim 1, wherein selecting the objective function for the modulation field includes:
   selecting a dorsal horn objective function to modulate dorsal horn tissue; and
   selecting a dorsal column objective function to modulate dorsal column tissue.

9. The method of claim 1, wherein:
   the volume of tissue has an activation function for an electrical modulation parameter that is proportional to an n-order spatial derivative of the electrical modulation parameter; and
   selecting the objective function for the modulation field includes selecting a constant objective function for the n-order spatial derivative of the electrical modulation parameter, the selected constant objective function to promote uniformity of a modulation response in the volume of tissue.

10. The method of claim 1, further comprising determining fractionalization values for each active contact to provide the selected modulation field that meets the selected objective function, wherein programming the neuromodulator with modulation parameters incudes programming the neuromodulator with the fractionalization values.

11. A method for modulating a volume of tissue to promote uniformity of a modulation response in the volume of tissue, wherein the volume of tissue has an activation function characterizing the volume of tissue's response to electrical modulation, the method comprising:
   selecting, using a user interface, a modulation field to electrically modulate the volume of tissue, wherein selecting the modulation field includes selecting an objective function for the modulation field that is specific to the volume of tissue and the activation function of the volume of tissue to promote the uniformity of the modulation response in the volume of tissue to the modulation field, wherein the objective function identifies characteristics of the modulation field for modulating the volume of tissue;
   determining fractionalization values for each active contact to provide the selected modulation field with the selected objective function, and programming a neuromodulator with the fractionalization values to promote the uniformity of the modulation response in the volume of tissue; and
   using the neuromodulator programmed with the fractionalization values to modulate the volume of tissue using the selected modulation field with the selected objective function specific to the volume of tissue and the activation function of the volume of tissue to promote the uniformity of the modulation response in the volume of tissue.

12. The method of claim 11, wherein determining fractionalization values for each active contact includes:
   estimating a unit field for each active contact using an electric field model, the estimated unit field being the field induced when the respective active contact is energized with an energy unit;
   determining weighted unit fields, including determining a perception threshold for each active electrode and calibrating the estimated unit field for each active electrode using the respective perception threshold;
   forming constituent source(s) for the active contacts, each of the constituent sources including an electrical contact to provide a source and another electrical contact to provide a sink;
   constructing a transfer matrix using the weighted unit fields for the constituent sources;
   solving for contributions from each constituent sources to provide the selected modulation field; and
   computing fractionalization values for each active contact from the solution for the constituent sources.

13. The method of claim 12, further comprising selecting active electrodes from a plurality of electrodes on at least one lead.

14. The method of claim 11, wherein selecting the objective function for the modulation field includes:
   selecting an objective function to modulate dorsal horn tissue; and
   selecting the objective function for the modulation field includes selecting a constant E objective function to modulate the dorsal horn tissue, or selecting a constant |E| objective function to modulate the dorsal horn tissue.

15. The method of claim 11, wherein selecting the objective function for the modulation field includes:
   selecting an objective function to modulate dorsal column tissue; and
   selecting a constant voltage to modulate dorsal column tissue.

16. A non-transitory machine-readable medium including instructions, which when executed by a machine, cause the machine to modulate a volume of tissue to promote uniformity of a modulation response in the volume of tissue, wherein the volume of tissue has an activation function characterizing the volume of tissue's response to electrical modulation, including:
   receive a selection of a modulation field to electrically modulate the volume of tissue, including receive a selection of an objective function for the modulation field that is specific to the volume of tissue and the activation function of the volume of tissue to promote the uniformity of the modulation response in the volume of tissue;
   determine modulation parameters for use by a neuromodulator to modulate the volume of tissue, using both the objective function and the activation function, to promote the uniformity of the modulation response in the volume of tissue, and
   program the neuromodulator with the modulation parameters to modulate the volume of tissue using the selected modulation field with the selected objective function specific to the volume of tissue and the activation function of the volume of tissue to promote the uniformity of the modulation response in the volume of tissue.

17. The machine-readable medium of claim 16, wherein the objective function includes a constant E objective function to modulate dorsal horn tissue.

18. The machine-readable medium of claim 16, wherein the objective function includes a constant |E| objective function to modulate the dorsal horn tissue.

19. The machine-readable medium of claim 16, wherein the objective function includes a constant |E| objective function to a constant voltage activation function to modulate dorsal column tissue.

20. The machine-readable medium of claim 16, wherein the instructions include instructions, which when executed by a machine, cause the machine to determine fractionalization values for each active contact to provide the selected modulation field that meets the selected objective function, wherein the fractionalized values for each electrode are used to deliver the selected modulation field with the selected objective function.

* * * * *